(12) United States Patent
Savelyeva et al.

(10) Patent No.: US 7,179,471 B2
(45) Date of Patent: Feb. 20, 2007

(54) MATERIALS AND METHODS RELATING TO FUSION PROTEINS AN IMMUNE RESPONSE

(75) Inventors: Natalia Savelyeva, Southampton (GB); Freda Stevenson, Southampton (GB)

(73) Assignee: Cancer Research Ventures Limited, London (GB)

( * ) Notice: Subject to any disclaimer, the term of this patent is extended or adjusted under 35 U.S.C. 154(b) by 144 days.

(21) Appl. No.: 10/416,290

(22) PCT Filed: Nov. 20, 2001

(86) PCT No.: PCT/GB01/05142

§ 371 (c)(1), (2), (4) Date: Oct. 27, 2003

(87) PCT Pub. No.: WO02/40513

PCT Pub. Date: May 23, 2002

(65) Prior Publication Data

US 2004/0072781 A1   Apr. 15, 2004

(30) Foreign Application Priority Data

Nov. 20, 2000 (GB) .................................. 0028319.2

(51) Int. Cl.
*A61K 39/12* (2006.01)
(52) U.S. Cl. ............................... 424/204.1; 424/278.1; 435/69.1
(58) Field of Classification Search ............ 424/204.1, 424/278.1, 199.1; 435/69.1, 6, 320.1
See application file for complete search history.

(56) References Cited

FOREIGN PATENT DOCUMENTS

EP   1 167 530 A2   1/2002
WO   91/15587      10/1991

OTHER PUBLICATIONS

Santa Cruz et al , PNAS, Jun. 1996, vol. 93, pp. 6286-6290.*
O'Brien, Graham, et al, "Rotavirus VP6 Expressed by PVX Vectors in *Nicotiana benthamiana* Coats PVX Rods and Also Assembles into Viruslike Particles", Virology 270, pp. 444-453, 2000, XP-002182558.
Dalsgaard, Kristian, et al, "Plant-derived vaccine protects target animals against a viral disease", Nature Biotechnology, vol. 1, Mar. 1997, pp. 248-252.
Hammond J.M., et al, "Expression of the potyvirus coat protein mediated by recombinant vaccinia virus and assembly of potyvirus-like particles in mammalian cells", Archives of Virology, 143, pp. 1433-1439, 1998.
Smolenska, Lisa, et al, "Production of a functional single chain antibody attached to the surface of a plant virus", FEBS Letters, 441, pp. 379-382, 1998.
Marusic, Carla, et al, "Chimeric Plant Virus Particles as Immunogens for Inducing Murine and Human Immune Responses against Human Immunodeficiency Virus Type 1", Journal of Virology, p. 8434-8439, Sep. 2001.

* cited by examiner

*Primary Examiner*—Ali R. Salimi
(74) *Attorney, Agent, or Firm*—Morgan, Lewis & Bockius LLP

(57) ABSTRACT

A nucleic acid construct is provided for delivery into living cells in vivo for inducing an immune response in a patient to an antigen; the construct directing the expression of a fusion protein, said fusion protein comprising said antigen and an adjuvant sequence derived from a plant viral coat protein. Methods for making such constructs, and methods of using such constructs for the treatment of infectious disease, cancer and B cell malignancy, are provided.

18 Claims, 20 Drawing Sheets

I) Vector with Myc Tag

```
                        rbs                M  K  Y  L  L  P  T  A  A
GCATGCAAATTCTATTTCAAGGAGACAGTCATAATGAAATACCTATTGCCTACGGCAGCC
       10        20        30        40        50        60
SphI PelB leader
     A  G  L  L  L  A  A  Q  P  A  M  A  Q  V  Q  L  Q  V  D
GCTGGATTGTTATTACTCGCGGCCCAGCCGGCCATGGCCCAGGTGCAGCTGCAGgtcgac
       70        80        90       100       110       110
                        SfiI                      PstI  SalI Myc Tag (TAG1)
     L  E  I  K  R  A  A  A  E  Q  K  L  I  S  E  E  D  L  N  *
CTCGAGATCAAACGGGCGGCCGCAGAACAAAAACTCATCTCAGAAGAGGATCTGAATTAA
       120       130       140       150       160       170
     XhoI        NotI

*
TAAGAATTC

EcoRI
```

II) Vector with Histidine Tag (pRH2)

```
                        rbs                M  K  Y  L  L  P  T  A  A
GCATGCAAATTCTATTTCAAGGAGACAGTCATAATGAAATACCTATTGCCTACGGCAGCC
       10        20        30        40        50        60
SphI PelB leader
     A  G  L  L  L  A  A  Q  P  A  M  A  Q  V  Q  L  Q  V  G
GCTGGATTGTTATTACTCGCGGCCCAGCCGGCCATGGCCCAGGTGCAGCTGCAGGTCGGC
       70        80        90       100       110       110
                        SfiI  NcoI                PstI L  E  I  K  R  A  A  A  H  H  H  H  H  H  *  *
CTCGAGATCAAACGGGCGGCCGCACATCACCATCATCACCATTAATAAGAATTC
       120       130       140       150       160
     XhoI        NotI                                    EcoRI
```

Figure 2

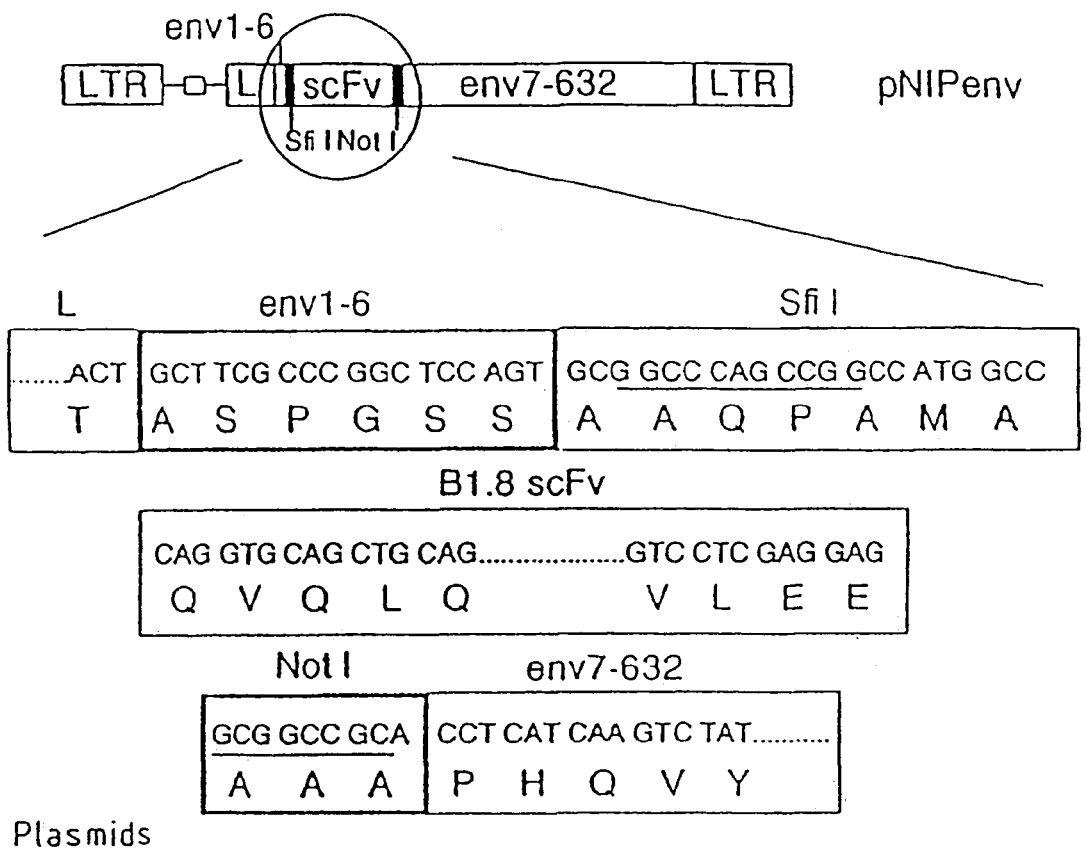
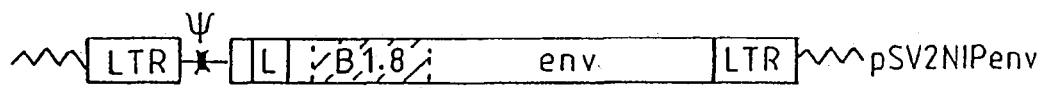
Figure 4 pVAC1
Hind III
AAG CTT AGC ATG GAC TGG ACC TGG AGG GTC TTC TGC TTG CTG GCT
 K   L   S   M   D   W   T   W   R   V   F   C   L   L   A
                 <----------------VH1 leader------------------

Sfi I
GTG GCC CCG GGG GCC CAC TCC CAG GTG CAG CTG CAG GTC GAC CTC
 V   A   P   G   A   H   S   Q   V   Q   L   Q   V   D   L
--------------->
         ^ Not I                                    Xba I
AGC GCT TGG CGT CAC CCG CAG TTC GCA AGC GCC GCA GCT TGG CGT CAC CCG CAG TTC
 S   A   W   R   H   P   Q   F

GAG ATC AAA CGG GCC GCA GCT TGG CGT CAC CCG CAG TTC
 E   I   K   R   A   A   A

GAG ATC AAA CGG GCC GCA GCT TGG CGT CAC CCG CAG TTC TCT AGA G....
 E   I   K   R   A   A   A

GAG ATC AAA CGG GCC GCA GCT TGG CGT CAC CCG CAG TTC
 E   I   K   R

CAG ATC AAA CGG GCC GCA GCT TGG CGT CAC CCG CAG TTC
 E   I   K   R

GGT GGT TAA TAA GAA TTG CTC
 G   G   *   *

1 GACGGATCGG GAGATCTCCC GATCCCCTAT GGTCGACTCT CAGTACAATC
  51 TGCTCTGATG CCGCATAGTT AAGCCAGTAT CTGCTCCCTG CTTGTGTGTT
 101 GGAGGTCGCT GAGTAGTGCG CGAGCAAAAT TAAGCTACA ACAAGGCAAG
 151 GCTTGACCGA CAATTGCATG AAGAATCTGC TTAGGGTTAG GCGTTTTGCG
 201 CTGCTTCGCG ATGTACGGGC CAGATATACG CGTATCTGAG GGGACTAGGG
 251 TGTGTTTAGG CGAAAAGCGG GGCTTCGGTT GTACGCGGTT AGGAGTCCCC
 301 TCAGGATATA GTAGTTTCGC TTTTGCATAG GGAGGGGGAA ATGTAGTCTT
 351 ATGCAATACA CTTGTAGTCT TGCAACATGG TAACGATGAG TTAGCAACAT
 401 GCCTTACAAG GAGAGAAAAA GCACCGTGCA TGCCGATTGG TGGAAGTAAG
 451 GTGGTACGAT CGTGCCTTAT TAGGAAGGCA ACAGACAGGT CTGACATGGA
 501 TTGGACGAAC CACTGAATTC CGCATTGCAG AGATAATTGT ATTTAAGTGC
 551 CTAGCTCGAT ACAATAAACG CCATTTGACC ATTCACCACA TTGGTGTGCA
 601 CCTCcaagct tagcatggac tggacctgga gggtcttctg cttgctggct
 651 gtggccccgg gggcccactc ccaggtgcag ctgcaggtcg acctcgagat
 701 caaacgggcg ccgcaagcg cttggcgtca cccgcagttc ggtggttaat
 751 aagaattggc cgctcGAGCA TGCATCTAGA GCTCGCTGAT CAGCCTCGAC
 801 TGTGCCTTCT AGTTGCCAGC CATCTGTTGT TTGCCCCTCC CCCGTGCCTT
 851 CCTTGACCCT GGAAGGTGCC ACTCCCACTG TCCTTTCCTA ATAAAATGAG
 901 GAAATTGCAT CGCATTGTCT GAGTAGGTGT CATTCTATTC TGGGGGGTGG
 951 GGTGGGGCAG GACAGCAAGG GGGAGGATTG GAAGACAAT AGCAGGCATG
1001 CTGGGGATGC GGTGGGCTCT ATGGAACCAG CTGGGGCTCG AGGGGGGATC
1051 CCCACGCGCC CTGTAGCGGC GCATTAAGCG CGGCGGGTGT GGTGGTTACG
1101 CGCAGCGTGA CCGCTACACT TGCCAGCGCC CTAGCGCCCG CTCCTTTCGC
1151 TTTCTTCCCT TCCTTTCTCG CCACGTTCGC CGGCTTTCCC CGTCAAGCTC
1201 TAAATCGGGG CATCCCTTTA GGGTTCCGAT TTAGTGCTTT ACGGCACCTC
1251 GACCCCAAAA AACTTGATTA GGGTGATGGT TCACGTAGTG GGCCATCGCC
1301 CTGATAGACG GTTTTTCGCC CTTTGACGTT GGAGTCCACG TTCTTTAATA
1351 GTGGACTCTT GTTCCAAACT GGAACAACAC TCAACCCTAT CTCGGTCTAT
```

Figure 7 (i)

```
1401 TCTTTTGATT TATAAGGGAT TTTGGGGATT TCGGCCTATT GGTTAAAAAA
1451 TGAGCTGATT TAACAAAAAT TTAACGCGAA TTTAACAAA ATATTAACGT
1501 TTACAATTTA AATATTTGCT TATACAATCT TCCTGTTTTT GGGGCTTTTC
1551 TGATTATCAA CCGGGGTGGG TACCGAGCTC GAATTCTGTG GAATGTGTGT
1601 CAGTTAGGGT GTGGAAAGTC CCCAGGCTCC CCAGGCAGGC AGAAGTATGC
1651 AAAGCATGCA TCTCAATTAG TCAGCAACCA GGTGTGGAAA GTCCCCAGGC
1701 TCCCCAGCAG GCAGAAGTAT GCAAAGCATG CATCTCAATT AGTCAGCAAC
1751 CATAGTCCCG CCCCTAACTC CGCCCATCCC GCCCCTAACT CCGCCCAGTT
1801 CCGCCCATTC TCCGCCCCAT GGCTGACTAA TTTTTTTTAT TTATGCAGAG
1851 GCCGAGGCCG CGAAATGACC GACCAAGCGA CGCCCAACCT GCCATCACGA
1901 GATTTCGATT CCACCGCCGC CTTCTATGAA AGGTTGGGCT TCGGAATCGT
1951 TTTCCGGGAC GCCGGCTGGA TGATCCTCCA GCGCGGGGAT CTCATGCTGG
2001 AGTTCTTCGC CCACCCCAAC TTGTTTATTG CAGCTTATAA TGGTTACAAA
2051 TAAAGCAATA GCATCACAAA TTTCACAAAT AAAGCATTTT TTTCACTGCA
2101 TTCTAGTTGT GGTTTGTCCA AACTCATCAA TGTATCTTAT CATGTCTGGA
2151 TCCCGTCGAC CTCGAGAGCT TGGCGTAATC ATGGTCATAG CTGTTTCCTG
2201 TGTGAAATTG TTATCCGCTC ACAATTCCAC ACAACATACG AGCCGGAAGC
2251 ATAAAGTGTA AAGCCTGGGG TGCCTAATGA GTGAGCTAAC TCACATTAAT
2301 TGCGTTGCGC TCACTGCCCG CTTTCCAGTC GGGAAACCTG TCGTGCCAGC
2351 TGCATTAATG AATCGGCCAA CGCGCGGGGA GAGGCGGTTT GCGTATTGGG
2401 CGCTCTTCCG CTTCCTCGCT CACTGACTCG CTGCGCTCGG TCGTTCGGCT
2451 GCGGCGAGCG GTATCAGCTC ACTCAAAGGC GGTAATACGG TTATCCACAG
2501 AATCAGGGGA TAACGCAGGA AGAACATGT GAGCAAAAGG CCAGCAAAAG
2551 GCCAGGAACC GTAAAAAGGC CGCGTTGCTG GCGTTTTTCC ATAGGCTCCG
2601 CCCCCCTGAC GAGCATCACA AAAATCGACG CTCAAGTCAG AGGTGGCGAA
2651 ACCCGACAGG ACTATAAAGA TACCAGGCGT TTCCCCCTGG AAGCTCCCTC
2701 GTGCGCTCTC CTGTTCCGAC CCTGCCGCTT ACCGGATACC TGTCCGCCTT
2751 TCTCCCTTCG GGAAGCGTGG CGCTTTCTCA ATGCTCACGC TGTAGGTATC
2801 TCAGTTCGGT GTAGGTCGTT CGCTCCAAGC TGGGCTGTGT GCACGAACCC
2851 CCCGTTCAGC CCGACCGCTG CGCCTTATCC GGTAACTATC GTCTTGAGTC
2901 CAACCCGGTA AGACACGACT TATCGCCACT GGCAGCAGCC ACTGGTAACA
2951 GGATTAGCAG AGCGAGGTAT GTAGGCGGTG CTACAGAGTT CTTGAAGTGG
3001 TGGCCTAACT ACGGCTACAC TAGAAGGACA GTATTTGGTA TCTGCGCTCT
```

Figure 7 (ii)

```
3051 GCTGAAGCCA GTTACCTTCG GAAAAAGAGT TGGTAGCTCT TGATCCGGCA
3101 AACAAACCAC CGCTGGTAGC GGTGGTTTTT TTGTTTGCAA GCAGCAGATT
3151 ACGCGCAGAA AAAAGGATC TCAAGAAGAT CCTTTGATCT TTTCTACGGG
3201 GTCTGACGCT CAGTGGAACG AAAACTCACG TTAAGGGATT TTGGTCATGA
3251 GATTATCAAA AAGGATCTTC ACCTAGATCC TTTTAAATTA AAAATGAAGT
3301 TTTAAATCAA TCTAAAGTAT ATATGAGTAA ACTTGGTCTG ACAGTTACCA
3351 ATGCTTAATC AGTGAGGCAC CTATCTCAGC GATCTGTCTA TTTCGTTCAT
3401 CCATAGTTGC CTGACTCCCC GTCGTGTAGA TAACTACGAT ACGGGAGGGC
3451 TTACCATCTG GCCCCAGTGC TGCAATGATA CCGCGAGACC CACGCTCACC
3501 GGCTCCAGAT TTATCAGCAA TAAACCAGCC AGCCGGAAGG GCCGAGCGCA
3551 GAAGTGGTCC TGCAACTTTA TCCGCCTCCA TCCAGTCTAT TAATTGTTGC
3601 CGGGAAGCTA GAGTAAGTAG TTCGCCAGTT AATAGTTTGC GCAACGTTGT
3651 TGCCATTGCT ACAGGCATCG TGGTGTCACG CTCGTCGTTT GGTATGGCTT
3701 CATTCAGCTC CGGTTCCCAA CGATCAAGGC GAGTTACATG ATCCCCCATG
3751 TTGTGCAAAA AAGCGGTTAG CTCCTTCGGT CCTCCGATCG TTGTCAGAAG
3801 TAAGTTGGCC GCAGTGTTAT CACTCATGGT TATGGCAGCA CTGCATAATT
3851 CTCTTACTGT CATGCCATCC GTAAGATGCT TTTCTGTGAC TGGTGAGTAC
3901 TCAACCAAGT CATTCTGAGA ATAGTGTATG CGGCGACCGA GTTGCTCTTG
3951 CCCGGCGTCA ATACGGGATA ATACCGCGCC ACATAGCAGA ACTTTAAAAG
4001 TGCTCATCAT TGGAAAACGT TCTTCGGGGC GAAAACTCTC AAGGATCTTA
4051 CCGCTGTTGA GATCCAGTTC GATGTAACCC ACTCGTGCAC CCAACTGATC
4101 TTCAGCATCT TTTACTTTCA CCAGCGTTTC TGGGTGAGCA AAAACAGGAA
4151 GGCAAAATGC CGCAAAAAAG GGAATAAGGG CGACACGGAA ATGTTGAATA
4201 CTCATACTCT TCCTTTTTCA ATATTATTGA AGCATTTATC AGGGTTATTG
4251 TCTCATGAGC GGATACATAT TTGAATGTAT TTAGAAAAAT AAACAAATAG
4301 GGGTTCCGCG CACATTTCCC CGAAAAGTGC CACCTGACGT C
```

Figure 7 (iii)

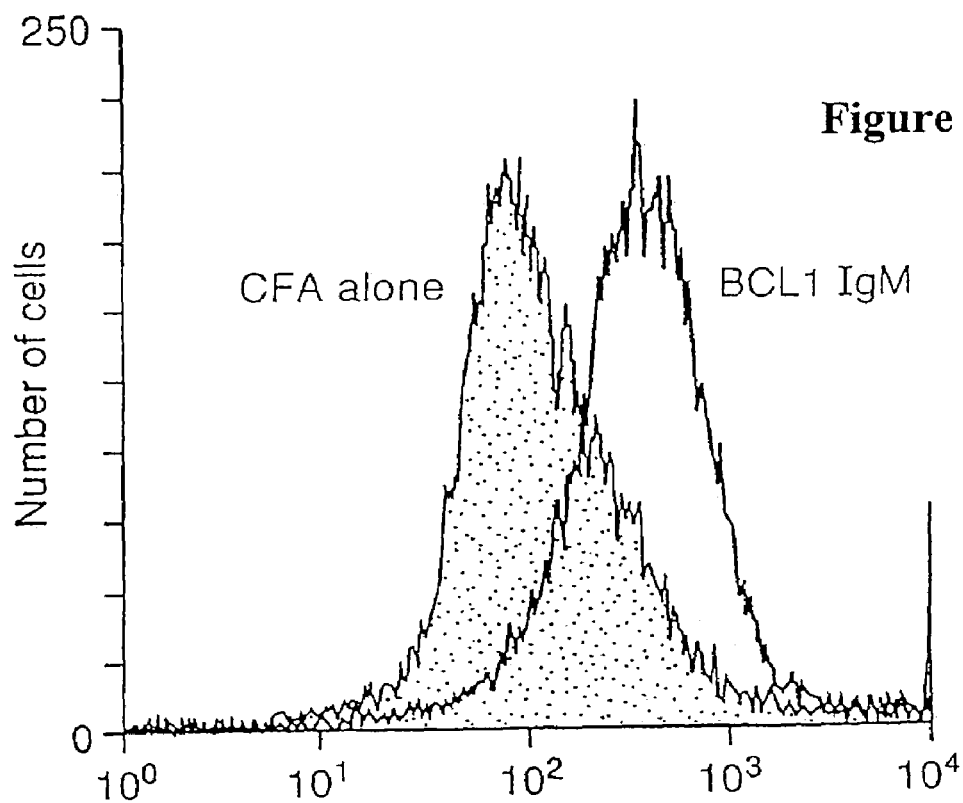
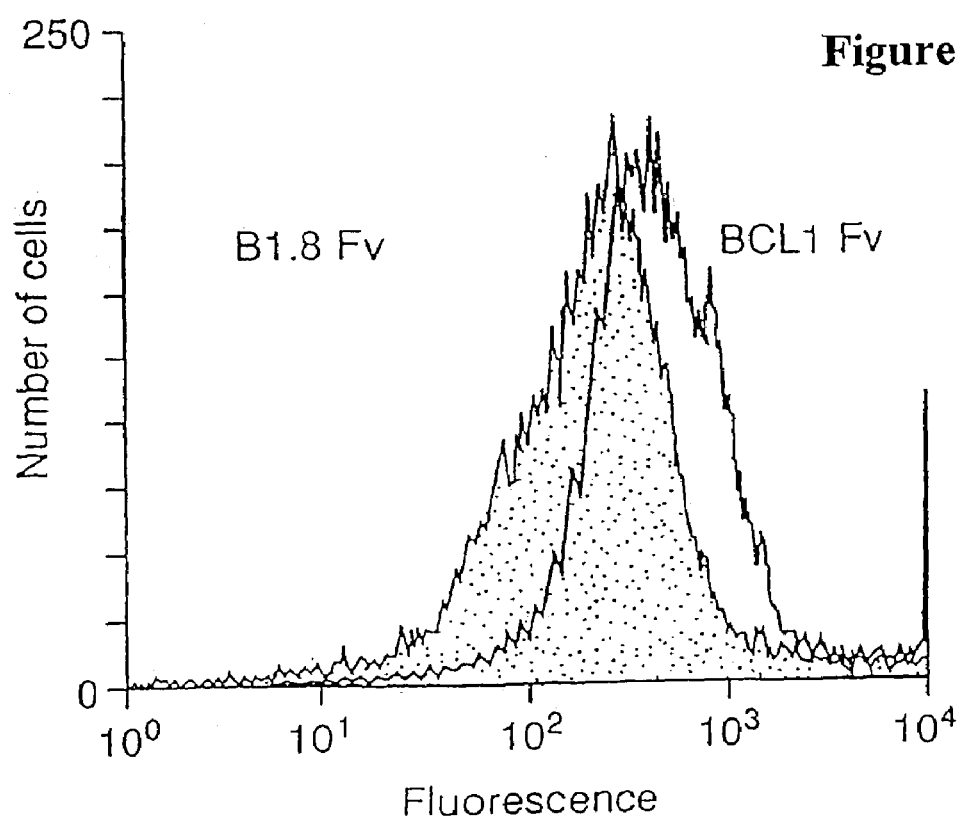

assembly of scFv-PVXCP fusions

Potato X virus particle

RNA

*Fig. 12* coat protein predicted structure of coat protein for PVX
131 (25kD)

labels: 102, 108, 170, 160, 37, 82, 72, 58, 70, 138, 33, 132, 14, 12, 4, 1, N, 22, 24, C 4 amino-acid linker (GPGP)

| scFv | PVXCP | pcDNA3 delivery cassette for PVXCP based DNA vaccine

A
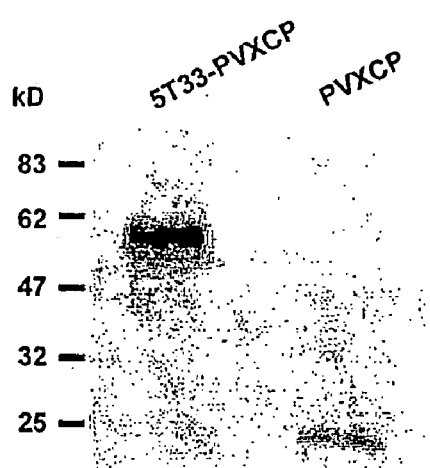
B
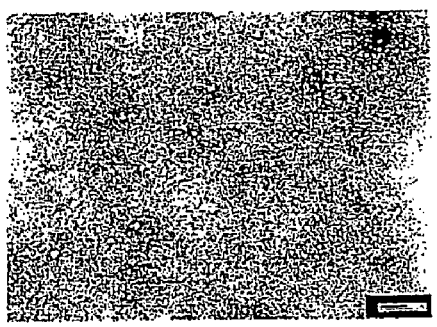
5T33-PVXCP
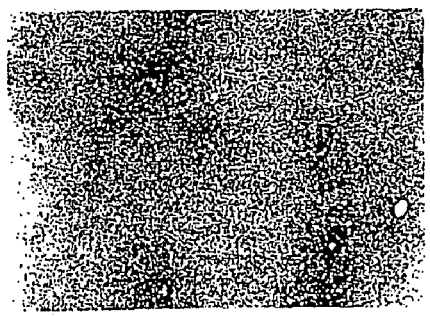
PVXCP
Figure 18

MATERIALS AND METHODS RELATING TO FUSION PROTEINS AN IMMUNE RESPONSE

FIELD OF THE INVENTION

This invention relates to a method of inducing an immune response in an individual and to novel compositions for performing the method of the invention and methods of making said compositions. Particularly, but not exclusively, the present invention relates to plant viral coat proteins as adjuvant sequences for inducing an immune response.

BACKGROUND OF THE INVENTION

The idiotypic determinants expressed on the cell surface immunoglobulin (Ig) of B-cell lymphomas can act as tumour-associated antigens (for review see George and Stevenson, 1989). As such they present an attractive target for therapy, notably for the administration of passive anti-idiotypic antibody to patients (Miller et al., 1982 New Engl. J. Med. 306, 517–522). Murine monoclonal antibodies (MAbs) raised against idiotypic determinants on B cell non-Hodgkin's Lymphomas (NHLs) have given limited benefit in human therapeutic trials. Partial and complete responses have been observed, but the murine MAbs tend to recruit human effector functions inefficiently and are themselves the target of a human anti-mouse antibody response. Also, outgrowth of surface Ig negative lymphoma cells has been observed following therapy (Levy et al., 1987 J. Immunol. Rev. 96, 43-; Bahler and Levy, 1992 PNAS 89, 6770–6774), although the complete loss of immunoglobulin expression is rare (Meeker, et al., 1985 New Engl. J. Med. 312, 1658–1665; Zelentz et al., 1990 Ann. Oncol. 2, 115–122). In light of these limitations. coupled with the cost and inconvenience of generating MAbs for individual patients, the approach has not been widely adopted. However, it is clear that anti-idiotypic antibodies do have therapeutic potential in lymphomas.

One alternative to passive anti-idiotypic serotherapy is active immunisation which aims to break tolerance and induce a strong anti-idiotypic antibody response in the patient. Since the response will be polyclonal, it is more difficult for the target B-cell to escape selection, and furthermore, the response will be present on a continuing basis, and so might be able to control residual disease. An additional advantage of this approach is that it also has the potential to stimulate T cell mediated immune responses against the lymphoma. Efforts to stimulate tumour immunity using modified tumour cell vaccines have met with limited success, but active immunisation with idiotypic Ig prior to tumour challenge has proved effective in suppressing model B-cell tumours (Stevenson and Gordon, 1983 J. Immunol. 130, 970–973; George et al., 1987 J. Immunol. 138, 628–634; Campbell et al., 1987 J. Immunol. 139, 2825–2833) in animals and to treat animals bearing incipient tumour (George et al., 1988 J. Immunol. 141, 2168–2174). Furthermore idiotypic immunisation with human Ig isolated from patients with lymphoma has been associated with sustained tumour regression (Kwak et al., 1992 New Engl. J. Med. 327, 1209–1215).

The problem is how best to present the antigen (the idiotypic antibody) to break tolerance and stimulate an effective anti-lymphoma immune response, and this remains a challenge. In addition, for lymphomas, which secrete little immunoglobulin, making the idiotype is a major problem. To make sufficient idiotypic antibody for immunisation heterohybridomas must be prepared by fusion with mouse cell lines and the antibody then purified (Carroll et al., 1985 J. Immunol. Methods 89, 61–67). The yield is frequently low and it must be subsequently confirmed that the fusion derives from the human B-cell tumour.

This latter problem has now been overcome: the use of recombinant DNA technology allows the $V_H$ and $V_L$ genes encoding the idiotypic determinant to be readily identified in patient biopsy material by PCR and sequencing (Hawkins et al, 1994 Blood 83:3279). These genes can be assembled as scFv for use as a DNA vaccine. This approach is based on the data coming from a range of infectious diseases where it is clear that DNA encoding sequences from pathogens can transfect cells directly and induce protective immune responses (Ulmer et al, 1993259:1745; Davis & Whalen 1995, In *Molecular and Cell Biology of Human Gene Therapeutics*. Ed. George Dickson. Chapman & Hall, p368).

In previous work, in a mouse model for lymphoma, the V-genes of the tumour idiotope were cloned and expressed as light and heavy chain fusion proteins in bacteria. The separate chains were then used as immunogens. However, the separate chains were denatured, and in any case were not co-expressed to provide the paratope of the antibody. Indeed the authors suggested that "future work on peptides with fixed configurations similar to epitopes present in the native protein may prove useful, as may the co-expression of both $V_H$ and $V_L$ genes in bacteria to produce a recombinant Fv protein" (Campbell et al., 1987, cited above). However, the authors did not teach how to isolate the V-genes of the idiotope. Nor did the authors teach how to combine the recombinant Fv fragments into a vaccine.

The present inventors have previously shown that nucleic acid constructs can be prepared which can be delivered into living cells in vivo and which can then induce an immune response to an idiotypic determinant present on a malignant B-cell. The construct encodes a fusion protein comprising the idiotypic determinant and tetanus toxoid fragment C (FrC). Indeed, the inventors have already specifically shown that genetic fusion of a lymphoma or a myeloma-associated antigen to the adjuvant sequence FrC of tetanus toxin induces a protective immunity in mice against challenge with lymphoma or myeloma when used as a DNA vaccine.

However, the human population is immune to FrC due to vaccination with Tetanus Toxoid. Therefore, when FrC-based vaccine is used in patients it will work in a setting of pre-existing immunity to FrC. So far the inventors have found that pre-existing antibody does not reduce the response to the DNA vaccine. However, it is possible that different immune pathways are activated in this situation.

SUMMARY OF THE INVENTION

Given the above, the present inventors have appreciated that there is a need to provide novel adjuvant sequences which overcome potential problems related to pre-existing immunity to C fragment of Tetanus Toxoid.

Plant viral coat proteins are highly immunogeneic molecules when injected into mammals. They have been used as protein vaccines when assembled into viral particles to present epitopes from infectious agents (Brennan, F. R. et al. Vaccine 17, 1846–1857 (1999). Such vaccines can induce high levels of neutralising antibodies and in some cases protection against challenge with the pathogen (Haynes, J. R. et al Bio/Technology 4, 637–641 (1986); Turpen, T. H. etal Bio/Technology 13, 53–57 (1995)). Potato virus X (PVX) was used to deliver systemically a functional single chain antibody fragment as a fusion to PVX coat protein into plants (Smolenska, L. et al FEBS letters 441, 379–382

(1998). However, PVX coat protein-based fusions were never delivered as DNA into mammalian cells. For DNA delivery, tobacco mosaic virus coat protein has been used to raise antibody against itself (Hinrichs, J. et al Journal of Virological Methods 66, 195–202 (1997)) but it has not been used as part of a fusion so as to induce an immune response against the other member(s) of the fusion construct.

The inventors have found that the potato virus X coat protein (PVXCP) works surprisingly well as an adjuvant in the construction of a DNA vaccine to induce protective immunity. Specifically, the inventors have genetically fused PVXCP to a lymphoma-associated antigen (scFv-A31) and used the construct for DNA vaccination of mice. This led to elevated antibody responses and protection against challenge with A31 lymphoma (see example 4, FIG. 14A). The inventors have further shown that this protection was mediated both by antibody to scFv-A31 and CD4 positive cells. This is in contrast with DNA vaccination using fusion of FrC to ScFv-A31, where such protection is mediated only by antibody to scFv. This finding could be significant when considering the disease to be treated, e.g. when the effectiveness of the treatment depends on a cellular response as opposed to an antibody response.

The inventors have also fused a myeloma-specific antigen scFv-5T33 to PVXCP. This construct was then used to vaccinate mice. This vaccination resulted in induction of antibody responses against scFv-5T33 and protection against challenge with 5T33 myeloma (see example 4, FIG. 14B). The inventors also determined that in this example the protection against myeloma is mediated by CD4 positive T cells.

Thus, the inventors have surprisingly shown that plant viral coat protein, e.g. PVXCP, can act as an adjuvant sequence for induction of protective immunity against tumour cells, for example, lymphoma and myeloma.

In a first aspect, the present invention provides a nucleic acid construct for delivery into living cells in vivo for inducing an immune response in a patient to an antigen; the construct directing the expression of a fusion protein, said fusion protein comprising said antigen and an adjuvant sequence derived from a plant viral coat protein.

In one embodiment, the antigen of the invention is derived from a pathogen, such as a virus (e.g. herpes simplex virus, human immunodeficiency virus etc) or a bacterium (e.g. staphylococcus, salmonella etc). However, the inventors have found that the present invention is particularly applicable where the antigen is a self or altered self polypeptide or is derived from a self or altered self polypeptide. The self or altered self polypeptide may be associated with an autoimmune disease or a cancer type. With regard to cancer, the self or altered self polypeptide is a tumour associated antigen such as an idiotypic determinant of a lymphocyte malignancy.

Thus, in preferred embodiment, the invention provides a nucleic acid construct for delivery into living cells in vivo for inducing an immune response in a patient to a self or altered self polypeptide; the construct directing the expression of a fusion protein, said fusion protein comprising the self or altered self polypeptide and at an adjuvant sequence from a plant viral coat protein.

Preferably, the adjuvant sequence promotes a helper T cell response when administered to a patient. More preferably, the adjuvant sequence comprises at least one T helper cell epitope.

In a preferred embodiment of the present invention, the plant viral coat protein is potato virus X coat protein (PVXCP). However, it will be apparent to the skilled person that other plant viral coat proteins of enveloped viruses may be used, e.g. tobacco mosaic virus coat protein. Many plant viral coat proteins are known and may be selected and tested by the skilled person. The adjuvant sequence is derived from the plant viral coat protein in that it contains nucleic acid sequence encoding a protein capable of promoting a T helper cell response. In a preferred embodiment, the adjuvant sequence comprises at least one T helper cell epitope.

Preferably the fusion protein will comprise a plurality of plant viral coat protein epitopes, both B and T cell. Typically the epitope sequence(s) from the plant viral coat protein will be placed on the carboxy side of the antigen.

It will be apparent to those skilled in the art that the composition, nucleic acid (DNA) vaccines and methods of the present invention can be used to either enhance or suppress the immune response to a particular antigen. Where the, antigen is a tumour associated antigen then it will clearly be desirable to enhance the immune response to the antigen so as to halt or reduce the growth of the tumour. Enhancement of the immune response is a preferred aspect of the present invention and preferably the enhancement is to tumour associated antigens in general, but particularly, idiotypic determinants in the immunoglobulin expressed on the surface of B cell malignancies, idiotypic determinants of T cell receptors (TCRs) expressed on the surface of T cell malignancies, mutated oncogenes or other self polypeptides expressed on the surface of tumours, and oncofoetal antigens.

For convenience, the following description will describe the invention in relation to idiotypic determinants. However, it will be apparent to the skilled person that the invention can be applied with ease to any antigen, e.g. antigen derived from pathogens such as viruses or bacteria, self or altered self polypeptides and, in particular, tumour associated antigen.

The idiotypic determinant is preferably present in the fusion protein in essentially the same conformation as that which it adopts on the surface of the patient's malignant B cells, thereby optimising the efficiency of the anti-idiotypic immune response induced by the construct. Conveniently this is achieved by expression of the idiotypic determinant within the context of a portion of an immunoglobulin (Ig) molecule or immunoglobulin-like molecule, such as a single chain Fv (scFv) fragment. The scFv fragment is particularly convenient, providing the necessary structural features of the idiotypic determinant with few extraneous amino acid residues. However, if desired additional amino acid residues could be included in the fusion protein, such as one or more constant domains (e.g. Syrengelas et al, 1996 Nature Medicine 2, 1038). Thus, for example, one could express the idiotypic determinant in the context of an entire immunoglobulin molecule.

In a preferred embodiment, the fusion protein is expressed with a leader sequence (recognised in human cells) which directs the fusion protein to the endoplasmic reticulum, where the leader sequence is cleaved from the fusion protein. A large number of suitable leader sequences are known including, for example, the leader sequences (such as that for $V_H1$ described below) found at the 5' end of human V genes. Such leader sequences have been found by the present inventors to increase the immunogenicity of the fusion protein. In principle, any other leader sequence is likely to exert an equivalent advantageous effect, but it is probable that those most similar to the natural immunoglobulin-type leader sequence will be optimal.

For the sake of convenience, the nucleic acid construct will preferably comprise a number of restriction endonuclease recognition sites. In particular, one or more such recognition sites may be located 5' of the sequence encoding the idiotypic determinant (conveniently between the optional leader sequence and the sequence encoding the idiotypic determinant), and one or more sites may be located 3' of the sequence encoding the idiotypic determinant (conveniently between the sequence encoding the idiotypic determinant and the epitope(s) from the plant viral coat protein). In this way, the same basic construct can readily be adapted to express different fusion proteins in which either the plant viral coat protein or, more preferably, the idiotypic determinant, may be altered. Thus sequences encoding idiotypic determinants from different patients can easily be introduced into the construct.

In a particular embodiment, this invention provides a vaccine nucleic acid which can be used to elicit an immune response against transformed human lymphocytes displaying an idiotypic marker, the nucleic acid encoding proteins comprising the heavy and light chain variable regions of an anti-idiotypic antibody displayed on surface of a malignant human B-cell an at least one T helper cell epitope from a plant viral coat protein, e.g. PVXCP.

In a second aspect, the invention provides a method of making a nucleic acid construct for raising an immune response against an antigen, the method comprising:

(a) identifying a nucleic acid sequence encoding the antigen;

(b) cloning the nucleic acid sequence; and (c) introducing the cloned nucleic acid into a vector, said vector allowing the protein to be expressed as a fusion with an adjuvant sequence derived from a plant viral coat protein.

The antigen may be derived from a pathogen such as a virus or a bacterium. However, in a preferred embodiment of the invention, the antigen is a self or altered self polypeptide, e.g. a tumour associated antigen.

In a further aspect, the invention provides a method of making a nucleic acid construct for treating a patient suffering from a B cell malignancy, the method comprising:

(a) identifying a nucleic acid sequence encoding an idiotypic determinant present on the malignant B cells of the patient by analysis of a sample of cells from the patient;

(b) cloning the nucleic acid sequence encoding the idiotypic determinant; and (c) introducing the cloned nucleic acid into a vector, which vector allowing the idiotypic determinant to be expressed as a fusion with an adjuvant sequence derived from a plant viral coat protein.

Preferably, the adjuvant sequence is able to promote helper T cell responses in vivo. More preferably, the adjuvant sequence comprises at least one T helper cell epitope from a plant viral coat protein.

Preferably, the plant viral coat protein is PVXCP or a part thereof, said part comprising at least one T helper epitope.

Conveniently the nucleic acid encoding the idiotypic determinant is cloned from a sample of the patient's cells by PCR. A large family of suitable generic PCR primers, capable of recovering nucleic acid sequences encoding essentially any B cell idiotypic determinant, is now available (Hawkins & Winter, 1992 Eur. J. Immunol. 22, 876). Typically the B cell malignancy is a lymphoma or a myeloma. Generally, the nucleic acid construct made by the method defined above will be in accordance with the first aspect of the invention.

In a third aspect, the invention provides a method of inducing an immune response in a patient, said method comprising the step of administering to said patient a nucleic acid construct in accordance with the first aspect of the invention defined above. Preferably, the nucleic acid construct forms part of a nucleic acid expression vector such that the adjuvant sequence and the antigen can be expressed in the patient. The nucleic acid sequence may be expressed in the patient without entering the patient's genome.

Preferably, the nucleic acid construct of the invention forms a naked DNA vaccine. Such a DNA vaccine is used to induce an immune response against the protein product encoded by the DNA.

DNA vaccination has been used successfully in the past as a way of inducing an immune response, see for example King et al., Nature Medicine 4: 1381, 1998.

In a further aspect, the invention provides a method of vaccinating a patient against an infectious disease, the method comprising administering to the patient a nucleic acid construct in accordance with the first aspect of the invention, in a physiologically acceptable medium, wherein the antigen is derived from a pathogen associated with said infectious disease. The method may be carried out on a patient with said infectious disease or on a subject at risk of contracting the infectious disease.

In a further aspect, the invention provides a method of treating a patient having or at risk of a cancer, comprising the step of administering to said patient a nucleic acid construct in accordance with the first aspect of the invention, in a physiologically acceptable medium, wherein the antigen is a tumour associated antigen associated with said cancer. The tumour associated antigen may well have been derived from the patients own cancer cells.

In a further aspect, the invention provides for a method of treating a patient suffering from a B cell malignancy and/or a method of inducing an immune response in a patient against a tumour associated antigen, the methods comprising administering to the patient a nucleic acid construct in accordance with the first aspect of the invention defined above, so as to induce an immune response to the idiotypic determinant present on the surface of the patient's malignant B cells. B cell lymphomas or myelomas are the conditions preferably treated by the method of the invention.

Preferably the nucleic acid sequence encoding the idiotypic determinant is cloned from samples obtained from the individual to whom it is delivered. Conveniently the nucleic acid sequence is delivered in unencapsidated form (i.e. not enclosed within a viral particle or other package). The nucleic acid may, however, be associated with the external surface of a package or particle (e.g. a liposome or a viral particle), which allows for the possibility of receptor-mediated delivery of the nucleic acid.

The fusion protein may direct the expression of the idiotypic determinant and the plant viral coat protein epitope alone. Alternatively the fusion protein may additionally comprise further immunomodulatory polypeptide sequences, such as other foreign immunogenic proteins, or cytokines. Indeed it may be valuable to use several antigenic fusion partners to help prevent the theoretical problem that the immune response to the highly immunogenic moiety of the fusion protein could ultimately overwhelm any response to the relatively weakly immunogenic idiotypic determinant. Other coat proteins of enveloped viruses and immunogenic cell surface or secreted proteins derived from any pathogenic organism or non-human species may be suitable for inclusion in the fusion protein.

An alternative modification is to design the nucleic acid construct so as to allow for the co-expression of the further immunomodulatory polypeptides as separate entities rather than as fusions with the idiotypic determinant/plant viral coat protein epitope. Less preferably, the method of the invention could employ the use of a separate nucleic acid construct to express the further immunomodulatory polypeptides.

A number of cytokines are known to improve aspects of antigen presentation and the direct delivery of expression vectors containing cytokine genes could enhance vaccine efficacy. Interferon gamma is one example that could be useful due to the property of up-regulating MHC expression (Gaczynska et al. 1993 Nature 365, 2, 264–267). Another polypeptide that could be expressed by the vaccine nucleic acid is granulocytelmacrophage-colony stimulating factor (GM-CSF). The relevant gene could be encoded on the same, or on a separate, vector and the amount of polypeptide expressed varied independently.

One advantage of the genetic approach to vaccination is that it potentially allows efficient use of the natural method of presenting antigen, which should therefore engage a wide range of effector systems. Moreover, manipulation and improvement of the response obtained should be relatively easy; for example, it may be possible to improve the efficiency of presentation of antigen to T cells by expressing molecules with costimulatory activity together with the immunogen. One important molecule involved in co-stimulation is B7, which interacts with CD28 expressed by T cells thereby providing accessory signals for T-cell activation (Galvin et al., 1992 J. Immunol. 12, 3802–3808). Vectors could be constructed which express both B7 and the idiotypic Ig. Sequences of both mouse and human B7 are published (Freeman et al., 1989 J. Immunol. 8, 2714–2722) and the genes may readily be cloned by PCR.

It is thus an optional feature of the present invention that the method further comprises the delivery of a second nucleic acid sequence to the individual, the second nucleic acid sequence directing the expression of a further immunomodulatory polypeptide for the purpose of further modulating the immune response to the idiotypic determinant. This second nucleic acid sequence may be comprised on the same nucleic acid molecule as the first nucleic acid sequence, or may be present on a second nucleic acid molecule.

Methods of introducing the nucleic acid construct into living cells in vivo are now well known to those skilled in the art. Conveniently the nucleic acid is simply injected as naked DNA into the patient (typically intramuscularly) as a mixture with a physiologically acceptable diluent, such as saline solution. Details of some suitable methods and preferred embodiments of the administration of the nucleic acid construct into a patient are described in U.S. Pat. No. 5,580,859 and 5,589,466. More involved methods of gene transfer include the use of viral vectors, encapsulating the DNA into liposomes, coupling of DNA to cationic liposomes or to the outside of viruses (for review see Miller, 1992 Nature 357, 45–46). These have the advantage of increased efficiency of transfer but, by comparison with direct injection of purified plasmid DNA, these alternative approaches are somewhat involved and raise more safety issues.

In a fourth aspect the invention therefore provides a composition for use in the method of treating a patient suffering from a B cell malignancy (according to the third aspect of the invention defined above) or a method of inducing an immune response against a tumour associated antigen in a patient, the composition comprising a nucleic acid construct directing the expression of a fusion protein, said fusion protein comprising an idiotypic determinant or a tumour associated antigen which is present on the malignant B cells of the patient and at least one T helper cell epitope from a plant viral coat protein, e.g. PVXCP, together with a physiologically acceptable diluent or carrier.

In a particular embodiment, the present invention entails the isolation of the V-genes from the tumour B-cells to express the idiotope (and paratope) of the tumour antibody. Thus, starting with a sample of B-cells from the patient, the rearranged V-genes of both heavy and light chains are amplified using the polymerase chain reaction and generic "universal" primers (Orlandi et al., 1989 PNAS 86, 3833–3837; Marks et al., 1991 J. Mol. Biol. 222, 581–597; see also Table 1, Seq. ID Nos. 1–48). The amplified V-genes are cloned and then sequenced (Sanger et al., 1977 PNAS 74., 5463–5467). Those from the malignant B-cells are identified as predominant repeated VH and VL gene sequences. In several patients, and for both heavy and light chains, it was possible to identify a common repeated sequence. The combination of the heavy and the light chains identifies the idiotope of the tumour (Example 1). In principle, it would also be possible to amplify and link the rearranged V-genes within the same cell (Embleton et al., 1992 Nucl. Acids Res. 20, 3831–3837) to identify a major combination of linked heavy and light chain sequences that identify the idiotope but here the VH and VL are separately identified and then linked by PCR assembly. The VH and VL genes are cloned into vectors for the expression of both V-domains as a functional antibody fragment, for example as a linked single chain Fv fragment (see below).

Ideally a vaccine should be capable of stimulating antigen-specific B cells, cytotoxic T lymphocytes (CTLs) and helper T cells. B cell stimulation requires that the target antigen should bind with sufficiently high affinity to specific antigen receptors (surface Ig) on the B-cell surface. Certain multivalent antigens can stimulate B cell proliferation directly but more often, and to provide an effective anamnestic response, there is a requirement for additional signals provided by helper T cells (see below). In the present invention, T cell help is recruited by expressing the idiotypic determinant as a fusion protein with at least one T helper cell epitope from a plant viral coat protein, preferably PVXCP.

The T cell receptors (TCRs) of CTLs recognise specific MHC class I-associated peptides displayed at the target cell surface. Such peptides are generally derived by processing of larger polypeptides or proteins manufactured within the target cell. Thus, for efficient CTL stimulation the target antigen should be synthesised intracellularly in MHC class I-expressing cells. The level of expression should be high enough to generate sufficient peptide to displace those self peptides which are normally bound (possibly with higher affinity) in the MHC peptide-binding groove (Ohno, 1992 PNAS 89, 4643–4647). Similar to antigen-specific B cells, for proliferation and increased cytotoxic capability, CTLs require additional signals (in the form of cytokines) following antigen recognition and these are provided by helper T cells.

CD4-positive helper T cells interact (via their unique TCRs) with specific cell surface MHC class II-associated peptides and such peptides are generally derived by proteolytic cleavage of protein antigens internalised by specialised antigen presenting cells (APCs). Macrophages, dendritic cells and B lymphocytes are amongst the cells which can present antigen in this way. Thus, B lymphocytes internalise and process antigen bound to their surface Ig and subsequently present MHC class II-associated derivative peptides. CD4-positive T helper cells recognising the surface peptide can then release various immunostimulatory cytokines and stimulate further B cell activation, proliferation and antibody production. Similarly, macrophages present at the site of a local inflammatory response can process phagocytosed antigen and stimulate cytokine release by T helper cells, leading to enhanced activation, proliferation and cytotoxicity of locally resident CTLs.

The vaccine antigen should therefore ideally be (1) synthesised intracellularly by MHC class I-positive host cells, (2) give rise to peptides which, when displayed by host cell class I MHC can stimulate a subset of host CTLs via their TCRs, (3) give rise to peptides which, when displayed by host cell class II MHC can stimulate a subset of host helper T cells via their TCRs, (4) be internalised and processed by host APCs including both macrophages and antigen-specific B cells, (5) be available in its native form for interaction with host B lymphocytes.

In a further specific embodiment, the invention provides for the expression of the rearranged VH and VL genes of the idiotype of the tumour antibody within mammalian cells, allowing the production of peptides for display on the cell surface in combination with host MHC, and for display (or secretion) of the paratope (as a folded antibody fragment), to trigger the production of anti-idiotypic antibodies. The antibody fragments could be introduced into mammalian cells by infection with a recombinant virus encoding the antibody fragments.

In principle, the antibody fragments could be provided with a signal sequence for their secretion or display on the surface of the infected (transfected) cell. Alternatively the fragments could be linked to another protein that is displayed on the surface of the cell, for example a viral coat protein, as described in Example 2. The antibody fragments (as single chain Fv fragments) are displayed in a functional form attached to the coat protein of a virus, indicating that they are also folded and in a native form on the surface of an infected cell (Russell et al., 1993 Nucl. Acids Res. 21, 1081–1085).

The antibody fragments could also be introduced into mammalian cells using nucleic acid encoding the antibody fragments. For example, a gene encoding a fusion protein between a viral coat protein (as above) and the antibody fragments may be used to immunise mice by direct injection (e.g. subcutaneous or intramuscularly).

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 2 shows the sequence of vectors used to express and purify scFv idiotypic immunoglobulin;

FIG. 4 is a schematic representation of the plasmid constructs pNipenv, pSV2 Nipenv, pSV2 Nip stop env, and pSV2 BCL env;

FIG. 5 shows the sequence of a HindIII-XbaI fragment of the vector pVAC1;

FIG. 7 shows the entire sequence of the vector pVAC1;

FIGS. 11a and 11b show the results of FACS analysis described in example 2;

FIG. 12 illustrates the assembly of scFv-PVXCP fusions.

FIGS. 18A and B show the results of analysis of scFv5T33-PVXCP and PVXCP proteins in experiments described in example 4. (In B, bar=200 nM.)

DETAILED DESCRIPTION OF THE INVENTION

EXAMPLES

Example 1

Figure 1:
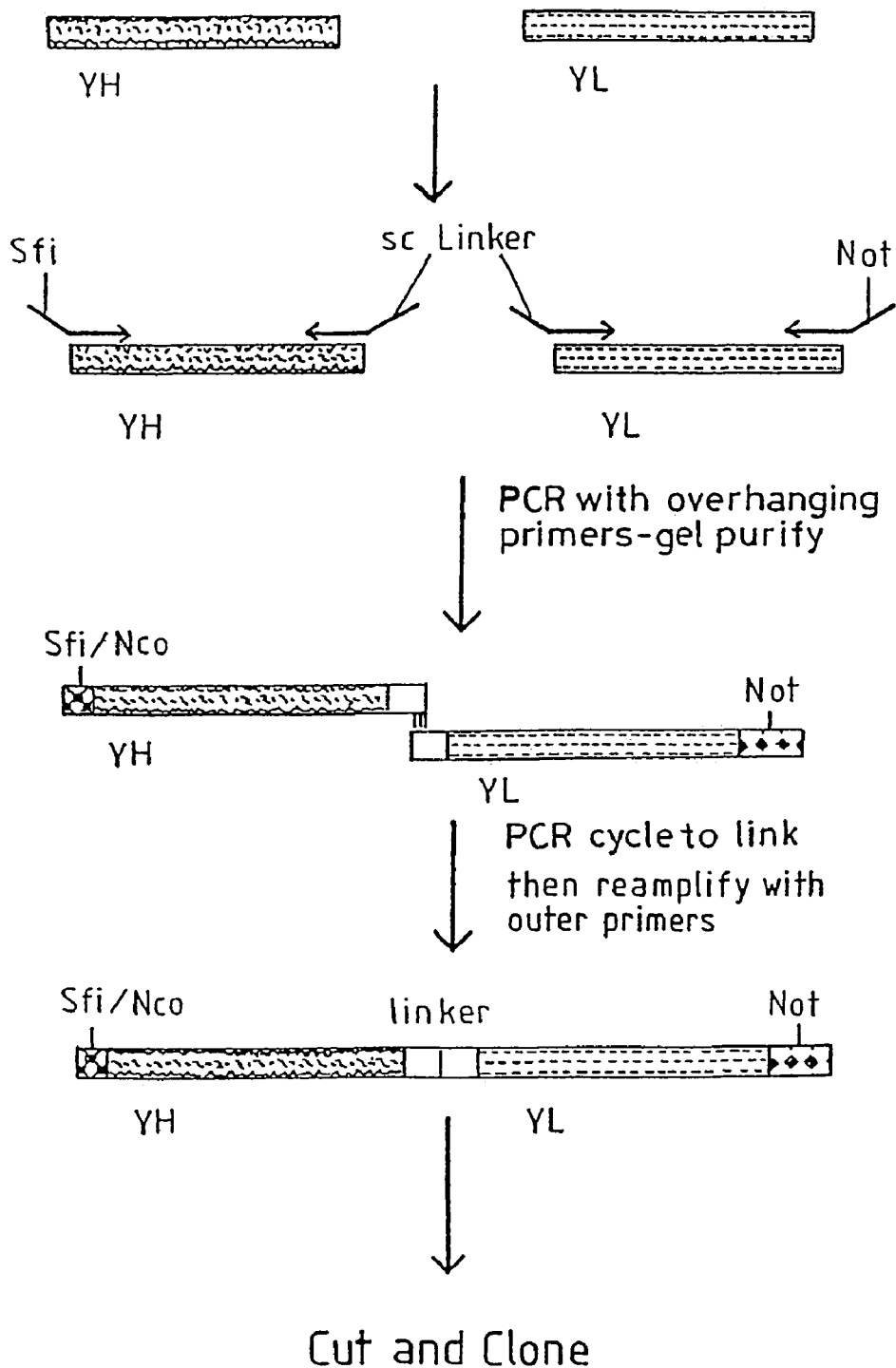
FIG. 1 is a schematic representation of the method of PCR assembly of DNA expressing scFv.

Indentification of V-Genes From Biopsies of B-Cell Lymphoma

Preparation of Biopsy Material.

Biopsy specimens were obtained from five patients with pathologically confirmed Follicular Lymphoma. They were obtained during routine diagnostic procedures. The light chains were identified as kappa or lambda by immunohistochemistry. As non-malignant controls, a small bowel lymph node from a patient with Crohn's disease and a sample of spleen from a patient undergoing splenectomy were obtained. Biopsy material was prepared as a single cell suspension and the cells subsequently frozen and stored at −70° C.

Preparation of DNA for PCR.

For PCR the DNA was prepared using a simple proteinase K/Tween 20 lysis method (Innis et al., 1990 PCR Protocols: A Guide to Methods and Applications; Academic Press Inc., p147). Briefly the cells were pelleted by centrifugation for 20 seconds at 13,000 rpm in a microcentrifuge. The cells were then washed twice with 1 ml PBS before resuspending at approximately $10^6$/ml in K-buffer (10 mM Tris.Cl (pH 8.3), 50 mM KCl, 1.5 mM $M_gCl2$, 0.5% Tween 20, 100 mg/ml proteinase K) and incubated at 56° C. for 60 minutes to lyse the cells and release DNA. The proteinase K was then inactivated by incubation for 30 minutes at 95° C. DNA thus released was used directly in the PCR reactions or stored for subsequent use at −20° C.

PCR Primers

PCR primers were designed to amplify re-arranged heavy chain kappa and lambda light chain genes. The 5' primers are based on framework 1 of the V-genes. The VH and Vk primers are similar to those described by Marks et al. (1991). However, for amplification from genomic DNA (as opposed to cDNA) the product was found to be cleaner if primers shortened by one base at the 3' end were used (data not shown). In addition, the number of primers used was reduced by combining similar primers as one consensus primer. With the exception of one change in the JH primers, to introduce a common BstEII site, changes were not made to introduce restriction sites.

Limited DNA sequence information was available on which to base the Vλ primers but primers were made to Vλ1, Vλ2, Vλ3 and Vλ4 families from the available sequence data (Songsivilai, et al. 1990 Eur. J. Immunol. 20, 2661–2666; Alexandre et al., 1989 Nucl. Acids Res. 17, 3975; Bernard et al. 1990 Nucl. Acids Res. 18, 7139; Chuchana et al., 1990 Eur J. Immunol. 20, 1317–1325). Other families are known to exist (Chuchana et al. 1990) but there were no nucleotide sequence data available and so primers were not made. J-region primers were made to be complementary to the genomic sequence of the germline J-regions for heavy chain (Ravetch et al., 1981 Cell 27, 583–591), kappa chain (Hieter et al., 1982 I. Biol. Chem. 257, 1516–1522) and lambda chain (Udey and Blomberg 1987 Immunogenetics 25., 63–70; Dariavach 1987 PNAS 84, 9074–9078; Bauer and Blomberg 1991 J. Immunol. 146, 2813–2820; Combriato and Klobeck, 1991 Eur. J. Immunol. 21, 1513–1522; Frippiat, 1990 Nucl. Acids Res. 18, 7134). The Jλ genes combine with their respective Cλ genes and thus since Cλ4, Cλ5 (Dariavach, 1987) and probably Cλ6 (Bauer and Blomberg, 1991; Combriato and Klobeck, 1991) are pseudogenes they should not appear as expressed protein. As a result primers to these Jλ genes were not made. By combining two J region primers, in all three Jl primers were made Jλ, Jλ2/3, Jλ7. Table 1 gives a full list of the primary PCR primers used in example 1.

PCR Amplification of Rearranged Immunoglobulin Variable Regions

The V-gene family and J-region primers were used as equimolar mixes of the individual primers shown in Table1. VHBACK and JHFOR mixes were used for the heavy chain PCR reaction. Similar mixes were used for kappa or lambda chain PCR amplification.

PCR amplification was performed in 50 ml volume using Hybaid Thermal Reactor (Hybaid). Reaction mixtures containing 20 pmol of each primer mix, 250 mM dNTPs (Pharmacia, Uppsala, Sweden) in 1×PCR buffer (Promega, 10 mM Tris.Cl [pH 8.8], 50 mM KCl, 1.5 mM $MgCl_2$, 0.1% Triton X-100). To minimise any risk of contamination extensive precautions were taken. The mixes were set up in a laminar flow hood in a room designated specifically for setting up PCR reactions. The samples were then UV treated for 5 minutes in a UV oven (Amplirad, Genetic Research, Dunmow, UK). The template (5 ml) was then added, the reaction mix was then overlaid with mineral oil (Sigma) and the sample heated to 94° C. for 5 minutes. At this stage Taq DNA polymerase (Promega), 2.5 units, was added. Amplification was performed using 35 cycles, 94° C. 1 min, 65° C., 1 min annealing; 72° C., 1 min elongation.

Amplified variable regions were analysed on a 1.5% LMP agarose/TAE gel and visualised with ethidium bromide. The band of size 320/350 base pairs was excised and purified using a GENECLEAN II kit (Bio101) according to the manufacturers instructions. At least two independent PCR amplifications of V regions were performed from the sample of every patient and the PCR of lymph node DNA was performed before the corresponding PCR from the hetero-hybridomas (which were also available).

Cloning and Sequencing of PCR Products

The T-vector cloning system described by Marchuk (Marchuk et al, 1991 Nucl. Acids Res. 19, 1154) was used. In brief, the vector was prepared from pBluescript II KS+ (Stratagene) by digestion with EcoRV (from NBL) to produce blunt ends and then treatment with Taq DNA polymerase (Promega) in PCR buffer (Promega) containing 2 mM dTTP at 70° C. for 2 hours. The purified V-gene PCR product was ligated into the T vector and transformed into competent E. coli—strain TG1 (Gibson, 1984 Ph. D. thesis, University of Cambridge, United Kingdom). Recombinant clones were identified by blue/white selection using isopropyl-β-thiogalactosidepyranoside (IPTG, Sigma). Random recombinant clones were picked and ssDNA prepared after superinfection with helper phage (MI3KO7, Stratagene) (Vieira and Messing, 1987 Methods Enzymol. 153, 3–11). The clones were sequenced by the dideoxy method (Sanger et al., 1977) using T7 DNA polymerase (Sequenase, USB, Cleveland, USA). A number of clones from each patient were sequenced and the sequences compared.

Assembly of Tumour V-Genes as scFv

The assembly method, illustrated in FIG. 1, is based on that described by Davis et al., (1991 Bio/Technology 9, 165–169). The assembly process uses a second set of primers. The VHSfiBAK primers encode SfiI cloning site and also hybridise to the original set of VHBAK primers. The scJHFOR and scVk/Vλ BAK primers hybridise to their respective initial primers but also encode the sc linker to allow production of a single chain Fv (scFv) (Huston et al., 1988 PNAS 85, 5879–5883).

The NotJk/IFOR primers hybridise to their respective initial primers but also include the NotI restriction site. These primers are also summarised in Table 1. The assembly is carried out in two stages. First the V-genes (heavy and light chains) were amplified from the sequencing template using the new set of oligonucleotides. The PCR mixture was made up as above but the primers used were only the relevant V-gene family and J-region primers identified by previous sequencing. Template was 100 ng of ssDNA sequencing template. The PCR conditions were 94° C. for 1 minute, 50° C. for 1 minute, 74° C. for 1 minute with 10 cycles of amplification. At the completion of the PCR the further dNTPs were added (5 ml of 2.5 mM stock solution) with Klenow polymerase (Boehringer; 2.5 units) and then incubated at 20° C. for 15 minutes to produce blunt ends.

Following this step the product was gel purified as above and resuspended in 25 ml water. Then 5 ml from the heavy and 5 ml from the light chain product were used in the assembly. For this process the PCR reaction was carried out in two steps. Initially no primers were added and the following cycles were used: 94° C. for 1 minute, 50° C. for 1 minute, 74° C. for 1 minute for 7 cycles to join the heavy and light chains. During the secondary PCR described above the heavy chain and light chain are tagged with primers encoding the single chain linker. This tag contains 15 nucleotides on each of the heavy and light chains complementary to each other and thus allows them to anneal to each other. During the extension reaction full length joined scFv molecules are formed. At the end of these 7 cycles the temperature is held at 94° C. for 3 minutes and the relevant outer primers (SfiVHBACK/NotJFOR) added for the "pullthrough" amplification. This amplification consists of 10 cycles: 94° C. for 1 minute, 74° C. for 2 minutes an serves to amplify the small amount of linked product formed.

Cloning for Expression, and Expression and Purification of scFv

After assembly the scFv was digested with SfiI/NotI as described (Marks et. al., 1992) and cloned into a scFv expression vector (Hawkins et al., 1992 I. Mol. BioI. 226, 889–896) based on pUC119 (Vieira and Messing, 1987). A new expression vector, pRH2, which has the Myc Tag replaced by a hexahistidine tag was made to allow purification using metal affInity chromatography. This was made by inverted PCR site directed mutagenesis (Hemsley et al., 1989 Nucl. Acids Res. 17, 6545–6551). The vectors are shown in FIG. 2 (Seq. ID Nos. 59–62).

To check for expression of full length scFv individual colonies were picked and grown for four hours with constant shaking in 1 ml 2×TY/0.1% Glucose/100 mg/ml Ampicillin at 30° C. At that stage IPTG was added to a final concentration of 1 mM and shaking continued for 18 hours. Supernatant was harvested by centrifugation at 13,000 rpm in a microcentrifuge for 5 minutes. The bacterial pellet was frozen at −20° C. for preparation of plasmid DNA and the supernatant was analysed by Western blotting using the 9E10 anti-Myc antibody (Ward et al., 1989 Nature. 341, 544–546). Plasmid DNA was then prepared from the bacterial pellet of colonies thus shown to express full length scFv. From this plasmid preparation the scFv was subcloned as an SfiI/NotI fragment into pRH2. One litre cultures of bacteria were grown with constant shaking in 2 litre flasks containing 2×TY/0.1% Glucose/100 mg/ml Ampicillin at 30° C. to an A600 nm of 0.9. At this stage IPTG was added to a final concentration of 1 mM and the incubation continued for a further 4 hours. The bacteria were then pelleted by centrifugation and the periplasmic fraction was prepared as described by Skerra et al., (1991 Bio/Technology 9, 273–278).

The scFv antibody fragment was purified from the periplasmic fraction utilising the hexahistidine tag. The method is based on that described by Skerra et al., (Skerra et al., cited above) but it was found that the use of six histidines and nickel rather than five histidines and zinc was preferable (data not shown). The periplasmic preparation from a 1 litre culture was loaded onto a 1 ml column of Chelating Sepharose Fast Flow (Pharmacia) previously coupled with nickel ions according to the manufacturers instructions. The column was then washed with 10 ml of PBS/1M NaCl (pH 7.2) followed by 5 ml PBS/1M NaCl/75 mM Imidazole (pH 7.2). The retained scFv was then eluted with 5 ml PBS/1M NaCl/300 mM Imidazole (pH 7.2) and collected as 1 ml fractions. The peak protein fractions were identified by determining the A280 nm and these were then dialysed against PBS before analysis by SDS-PAGE.

PCR, Cloning and Sequencing of V-Genes From Follicular Lymphoma and Normal Lymph Node The PCR amplification from the DNA of biopsy specimens was successful in all cases apart from the lambda light chain from patient number 5. A number of clones from each patient were sequenced. Analysis of the sequences derived from the reactive lymph node and from the normal spleen revealed that there were no repeated sequences. From each of the tumour bearing lymph nodes there were single repeated sequences. A summary of the sequencing results is shown in Table 2. Amongst the repeated sequences there were up to two base changes which were presumed to result from PCR errors. Nevertheless a consensus sequence was readily apparent and in each case there were clones with this consensus sequence. To confirm the sequence a second independent amplification was performed and further V-genes sequenced. The same consensus sequence was identified. The repeated V-gene sequences suggest clonal expansion and thus identifies the tumour V-gene. For three of the five tumour biopsies analysed here a heterohybridoma was available. PCR amplification, cloning and sequencing confirmed the sequence identified direct from the lymph node.

The absolute percentage of the tumour derived V-gene varied and there are several reasons for this. First, the biopsies vary in the degree of tumour infiltration (although in all cases examined here malignant B-cells comprise >50% of the total cells present). Second, the primers will vary in the efficiency with which they amplify any particular gene— in extreme cases as with the lambda light chain in patient 4 a chain may not amplify at all. Third, some pseudogenes can be amplified by these primers and this may reduce the overall percentage of tumour derived V-genes.

Assembly, Expression and Purification

The use of PCR assembly avoids the use of multiple restriction enzymes which may cut V-genes at internal sites. This process used here appears efficient and does not require the separate preparation of a linker fragment (Clackson et al., 1991 Nature 352, 624–628). To check the assembly process the linked product was cloned into an expression vector which included the Myc Tag (FIG. 2). Randomly picked clones were grown up and induced as previously described (Hawkins and Winter, 1992). Western Blotting using a monoclonal antibody, 9E10, against the Myc Tag (Ward et al., 1989) demonstrated that 80% of the clones correctly expressed. For ease of purification the scFv fragment was subcloned into the expression vector pRH2 containing a hexahistidine tag. A clone from patient 5 was grown up in a 1L volume the scFV fragment purified from the periplasm. The yield was estimated as 0.5 mg/L/OD600 based on an A280 nm of 1.4 for a 1 mg/ml solution.

Example 2

Construction of a Fusion Protein

Plasmid Construction

The BamHI/ClaI env fragment (nt 6537–7674, nt numbering from Shinnick et al, 1981 Nature 293, 543–548) from pCRIP (gift from O. Danos, Danos & Mulligan 1988 PNAS 85, 6460–6464) was cloned into the BamHI/ClaI backbone fragment of pZipNeoSV (X) (gift from R. Mulligan, Cepko et al., 1984 Cell 37, 1053–1062) to generate an intermediate plasmid penvBam/Cla.

A SfiI/NotI cloning site was introduced beyond the leader peptide sequence between codons corresponding to the 6th and 7th amino acids (from the N-terminus) in the mature MoMLV env polypeptide. The oligonucleotide pair envNotrev (5'-CTG CAG GAG CTC GAG ATC AAA CGG GCG GCC GCA CCT CAT CAA GTC TAT AAT ATC-3', Seq ID No. 49, complementary to MoMLV env nts 5894–5914 with a 33nt 5' overhang encoding a Not1 site and 21nt complementary to the 5' tail of envSfifor) and envseq 7 (5'-GCC AGA ACG GGG TTT GGC C-3[1], Seq ID No.50, reverse complement of MoMLV env nts 6581–6600) was used to prime amplification (from plasmid pCRIP) of a 739 bp fragment downstream ofenv codon 6. A second oligonucleotide pair, envSfifor (5'-TTT GAT CTC GAG CTC CTG CAG GGC CGG CTG GGC CGC ACT GGA GCC GGG CGA AGC AGT-3 ', Seq. ID No.51, reverse complement of MoMLV env nts 5873–5893 with a 36nt 5' overhang encoding a SfiI site and 21nt complementary to the 5' tail of envNotrev) and revMLVpol (5'-AAT TAC ATT GTG CAT ACA GAC CC-3 ', Seq ID No.52, complementary to MoMLV pol nts 5277-5249) was used to prime amplification (from pCRIP) of a 702 bp fragment upstream of env codon 7. Amplifications were carried out using Vent polymerase and reactions were subjected to 15 PCR cycles at 94° C. for 1 min, 60° C. for 1 min and 72° C. for 1 min. The complementary 21nt tails of the 702 and 739 bp gel-purified PCR products allowed. PCR linkage to generate an env gene fragment incorporating a SfiI/NotI cloning site at the desired position. The two fragments were mixed and subjected to three PCR cycles (94° C., 40° C., 72° C. for 1, 1, and 2 minutes respectively) followed by 17 further cycles of amplification (94°, 60°, 72° for 1, 1 and 2 minutes respectively) after addition of oligonucleotides envseq7 and Bglenvrev (5'-TAA TCA CTA CAG ATC TAG ACT GAC ATG GCG CGT-3 ', Seq ID No.53, complementary to MoMLV pol nucleotides 5766 to 5785 with the 5' tail incorporating a BglII restriction site).

Figure 3:
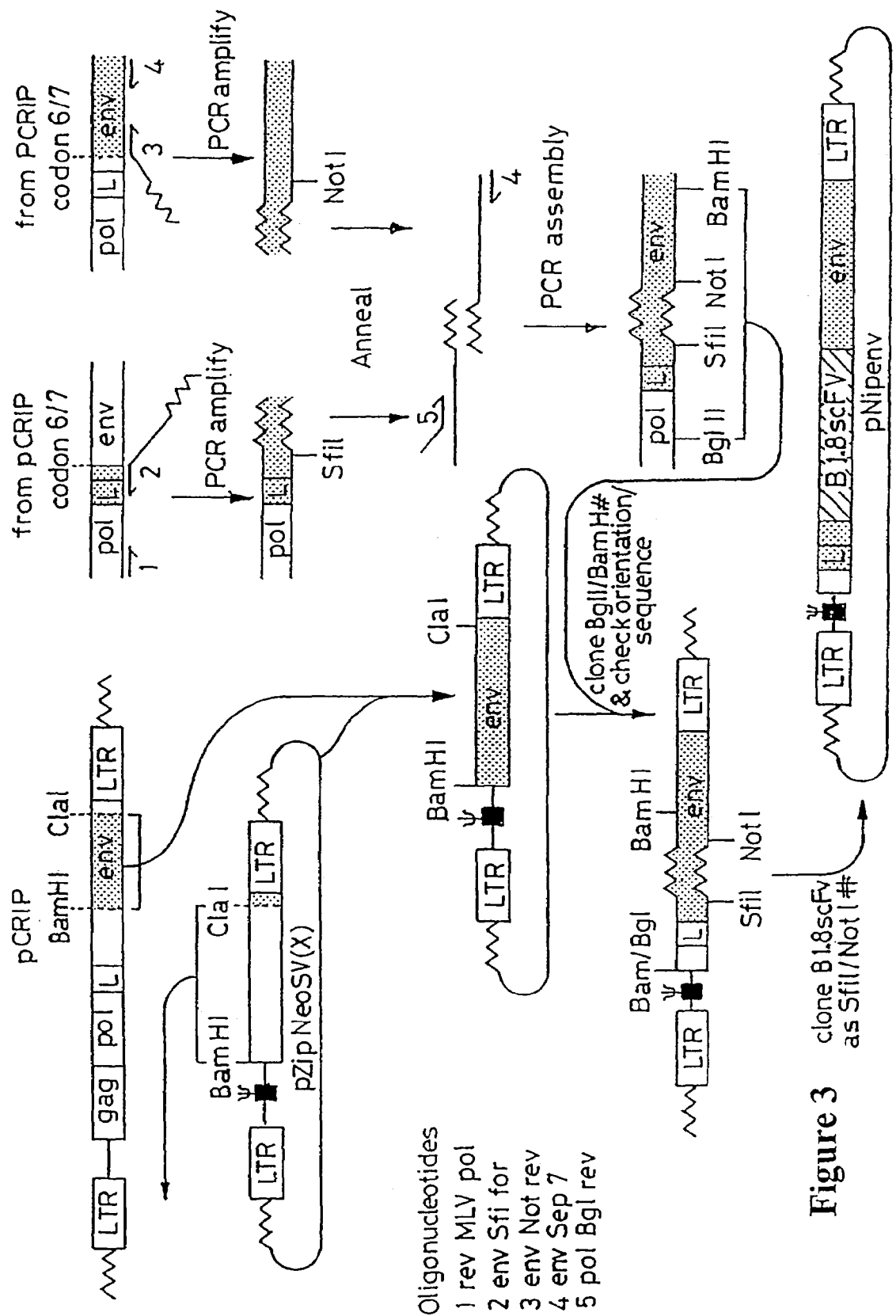
FIG. 3 is a schematic representation of the method used to produce plasmid pNipenv.

The product, a 905 bp fragment, was digested with BglII and BamHI and cloned in forward orientation into the BamHI site of penvBam/Cla (see above) giving the plasmid pSfi/Notenv. Correct assembly of this plasmid was confirmed by restriction analysis and dideoxy sequencing (Sanger et al., 1977 PNAS 74., 5463–5467). A functional B1.8 scFv antibody was then subcloned from prokaryotic expression vector (Hawkins et al., 1992 J. Mol, Biol. 226, 889–896) as an Sfi/lNotI fragment into the SfiI/NotI cloning site of pSfi/Not.Env to generate the plasmid pNIP.env (FIG. 3). The sequence across the junctions of pNIPenv is shown in FIG. 4 (Seq. ID No.63 to 66, including translation of nucleotide sequence).

Finally, the modified retroviral envelope expression cassette was subcloned as a HindIII/EcoRI fragment into a modified pSV2Neo plasmid (a gift from Ashok Venkitaraman, MRC Centre, Cambridge) to generate the plasmid pSVNIPenv (FIG. 4).

Cell Transfection

NIH3T3 fibroblasts and the ecotropic retroviral packaging cell line psi2 (Mann et al., 1983 Cell 33, 153–159) were maintained in DMEM/100% FBS supplemented with 60 μg/ml benzylpenicillin and 100 μg/ml streptomycin at 37° C. in atmosphere of 5% $CO_2$. The cells were replated twice weekly using EDT A without trypsin to disrupt the monolayer.

Plasmid pNIPenv was transfected (with pDCneo, a plasmid containing a neomycin resistance marker) into psi2 cells by calcium phosphate precipitation. Briefly, $2\times10^5$ cells were plated in 90 mm tissue culture plates (Nunc), cultured overnight, washed and fed with 10 mls new medium. 10 μl plasmid DNA and 50 μl 2M $CaCl_2$ (0.2 μm-filtered) were diluted in sterile water to a volume of 400 μl. The $CaCl_2$/DNA mix was added drop wise to an equal volume of 0.2 μm-filtered 2×HEPES-buffered saline (280 mM NaCl, 10 mM KCl, 1.5 mM $Na_2HPO_4.2H_2O$, 12 mM dextrose, 50 mM HEPES, pH adjusted to 7.05 with 0.5N NaOH) and left to stand for 20 minutes at RT. The transfection solution (800 ml) was added to the cells which were cultured for 16 hrs, washed and refed. G418 selection (1 mg/ml) was commenced 24 hrs later and continued for approximately 2 weeks.

Transfected colonies expressing surface B1.8 single chain antibody were identified by panning with NIP.BSA-coated beads. Briefly, Tosyl activated paramagnetic beads (Dynal, Oslo, Norway, Prod. no. 14004) were coated with NIP10.BSA (approximately 10 NIP-caproate-O-succinimide molecules coupled to each bovine serum albumin molecule, Hawkins et al., 1992), washed extensively in PBS and blocked with DMEM/10% FBS. 90 mm tissue culture plates containing up to 50 G418-resistant psi2 colonies were rocked gently for 1 hr at 40° C. followed by 1 hr at room temperature with $2\times10^7$ (50 μl) beads in 5 mls DMEM/10% FBS. After 5 washes in PBS, positive colonies (heavily coated with paramagnetic beads) were easily identified and were transferred individually for further expansion, cryopreservation and harvest of cell supernatants.

Therefore it was shown that the specificity of the antibody is displayed on the surface of the cells, and therefore that the antibody is folded.

Construction of a Soluble Protein Expression Vector

To create a soluble expression vector a stop codon and frame shift mutation were inserted between the antibody gene and the 3' portion of the MoMLV Envelope gene. The B1.8 scFv fragment was PCR-amplified (10 cycles, 94° C. 1 min, 55° C. 1 min, 74° C. 1 min) using SfiVHBAK (5'-TAC TCG CGG CCC AAC CGG CCA TGG CCC AGG TSM ARC TGC AGS AGT C-3 ', Seq ID No.54) and a forward primer Not.STOP (5'-AAC AGT TTC TGC GGC CGC CTC CTC AGA GGA C-3 ', Seq ID No.55) encoding the nucleotide insertion to create a stop codon and frameshift 5' of the NotI site. The fragment was then digested with SfiI/NotI and cloned into pSfi/Not.Env to create the plasmid pNIPstop (FIG. 4). Plasmid pSVBCLenv (FIG. 4) was derived from pSVNIPenv by replacing the B1.8 scFv with a control scFv gene which was PCR-cloned from the BCL1 mouse lymphoma. VH and Vλ genes were PCR cloned and assembled from BCL-derived DNA using standard protocols.

Preparation of Plasmid DNA

Plasmids were amplified in *E. coli* strain TG1 (Gibson, 1984), extracted by alkaline lysis and column purified using the Promega Magic Maxipreps™ DNA purification system (Promega, Madison, Wis., USA). The DNA was eluted in water. The purity of the plasmid prep was confirmed by agarose gel electrophoresis and by measuring the A260 nm/A280 nm ratio (in all cases the ratio was >1.7). The purified plasmid was stored at −20° C. Prior to use the plasmid was adjusted to 160 mg/ml in 200 mM NaCl.

Preparation of B1.8 scFv Protein

For bacterial expression, the B1.8 scFv gene was cloned as a PstI/NotI fragment into the vector pRH2, which links a tail of six histidines to the C-terminus of the scFv and was derived by inverse PCR mutagenesis. This plasmid was transformed into *E. coli*, strain TG1 and the scFv protein expressed and purified on an NP-sepharose column as previously described (Hawkins and Winter, 1992 Eur. J. Immunol. 22, 867–870). The purified protein was shown to bind strongly to NIP-BSA using a previously described BLISA (Hawkins and Winter, 1992). As a negative control scFvDl.3 (Hawkins et al., 1992) was cloned into the expression vector pRH2 and expressed and then purified on a lysozyme column as described by Hawkins et al., 1992, (cited previously).

Vaccination protocol Male BALB/c mice 10 weeks of age were used for immunisation. Pre-immunisation blood samples were obtained by tail bleeds. The blood was centrifuged at 13,000 rpm for 2 minutes in a microcentrifuge to separate the serum. The serum then stored at −20° C. for subsequent assay. Two groups of mice were immunised some with DNA and some with protein. The two groups were immunised as described below.

a) Protein vaccine: B1.8 scFv protein was adjusted to a concentration of 250 mg/ml in PBS and mixed with an equal volume of CFA. Mice were challenged subcutaneously with 100 ml of this vaccine (12.5 mg scFv) at two separate sites. Identical boosts were administered two and four weeks later. 200 ml tail bleeds were obtained 10 days after the final boost. Blood samples were processed as above.

b) DNA vaccine: Two groups of three mice were challenged with 50 ml (8 mg) DNA, either subcutaneously (sc) in both flanks, or by the intramuscular (im) route (right and left quadriceps, total DNA for each mouse 16 mg). Two identical booster inoculations were given at one week intervals. 200 ml tail bleeds were obtained immediately prior to the first, second and third challenge and one week after the final boost. Serum was separated and stored as above.

Analysis of Immune Response

Individual flat-bottomed wells in flexible 96 well assay plates (Falcon 3912 MicroTest III) were coated with B1.8.His or control (Dl.3.His anti-lysozyme) scFv protein at 25 mg/ml overnight in PBS at room temperature. The use of the histidine tagged scFv to coat the plates has been found to result in more of the protein retaining its antigen binding capacity. Plates were washed x 3 with PBS, blocked for 2 hrs at 37° C. with 3% BSA in PBS and washed x 3 in PBS. Test serum was added (diluted 1:100 or 1:1000 in PBS/3% BSA) and incubated for one hour at room temperature. Plates were washed x 3 in PBS and incubated for one hour at room temperature with a second layer HRP-conjugated polyclonal goat anti-mouse Fc antibody at 1:1000 dilution (Sigma, cat. no. AO 168) Plates were washed x4 in PBS, developed with ABTS and the A405 nm measured after 30 minutes using a Thermomax™ microplate reader (Molecular devices, Menlo Park, USA).

Results

Immune Response to Protein Vaccine

It was first sought to establish whether mice could mount an effective anti-idiotypic humoral immune response when challenged with a scFv murine antibody in CFA. Six mice were challenged subcutaneously with 25 mg of the B1.8 anti-NIP scFv in CFA, with booster doses two and four weeks later. Ten days after the final challenge; serum from these animals contained insufficient anti-B1.8 antibody to give a positive BLISA signal at 1:100 dilution of the serum.

Immune Response to DNA Vaccine

Plasmid pNIPenv (FIG. 3, see materials and methods for details of construction) encodes a chimeric fusion protein consisting of the ecotropic MoMLV envelope polypeptide Pr80env with a scFv anti-NIP antibody fragment (Kd $4\times10^{-8}$M) inserted 6 amino acids from the N-terminus. The 33 amino acid MoMLV env leader sequence is retained, without disruption of the leader cleavage site. As well as the 6 N-terminal amino-acids from the MoMLV envelope protein the scFv also has a further 6 amino-acids derived from the pelB leader remaining at the N-terminus. Expression is driven from promoter/enhancer sequences in the 5' MoMLV long terminal repeat (LTR). Polyadenylation signal sequences are provided by the 3' MoMLV LTR. When transfected into mouse fibroblasts (described above), it was found that pNIPenv gave stable cell-surface expression of functional B1.8 scFv in fusion with the MoMLVenv protein.

Mice were primed via the subcutaneous (three mice) or intramuscular (three mice) route with 16 mg of pSVNIPenv in 200 mM NaCl, with booster doses one and two weeks later. Control mice were vaccinated pSVBCLenv. Pre-vaccination, pre-booster and one week post-vaccination serum samples were tested by ELISA for a humoral response to B1.8scFv. Prior to the second booster, anti-B1.8 scFv antibodies were detected at 1:100 dilution of the serum in three of the six pSVNIPenv-vaccinated mice, two inoculated im and one sc. One week after the second booster, all six mice had easily detectable anti-B1.8 scFv antibodies which did not cross-react with the Dl.3 scFv. Sera from control pBCLenv-vaccinated mice remained negative in the anti-B1.8 ELISA.

Anamnestic Response to Protein Vaccine after DNA Vaccine

After 8 weeks, anti-B1.8 antibody titres had fallen in the pSVNIPenv immunised mice. At this point the three mice, originally inoculated intramuscularly with pNIPenv, were challenged intravenously with 20 mg purified B1.8 scFv protein in PBS. Five days later, serum from these mice contained a greatly increased titre of anti-B1.8 antibodies—the average rise was 12 fold and all had antibodies clearly detectable at 1:1000 dilution.

Boosting with Soluble scFv Expression Vector (pNIPstop)

To test whether boosting with a soluble protein expression vector would also boost the antibody titre, mice were inoculated with pNIPstop. Ten weeks after the primary immunisation, the three mice immunised subcutaneously with pNIPenv were inoculated with 8 mg sc and 8 mg im in 200 mM NaCl. Five days after boosting, test bleeds were obtained and assayed for antibody activity The serum titre increased an average of 10 fold and again all were now positive at 1:1000 dilution.

Comparison of Soluble pNIPstop and pNIPenv in Generating Primary Immune Response To demonstrate the importance of the fusion protein to enhance the immune response the inventors carried out a control experiment to compare the efficacy of two vectors at stimulating a primary immune response. Two groups each consisting of two BALB/c mice were used as before. Serum was obtained by tail bleed as before and then the mice were inoculated weekly x3 with the appropriate plasmid. Twenty-eight days after the start of immunisation serum was again obtained following tail bleeds and assayed for anti-B1.8 activity. 2/2 from the group inoculated with the pNIPenv plasmid were positive at 1:100 dilution and 2/2 in the pNIPstop group were positive. Clearly the env tag is not necessary to stimulate an immune response.

Confirmation That Immune Response Recognises the Native Antigen.

A group of five mice immunised four times with DNA (pSV2-BCL1) encoding the unfused BCL1 scFv fragment also generated humoral responses to the idiotype, as detected by binding to the BCL1 IgM fragment in an ELISA (not shown). Moreover, as a clear demonstration of their ability to recognise native antigen in the form required for therapy, these anti-idiotypic antisera were shown by FACS analysis to bind to lymphoma cells bearing surface BCL1 Ig. BCL1 cells were pre-incubated with serum at a 1:20 dilution before staining with FITC conjugated anti-mouse IgG (Sigma) and followed by FACS analysis. Indeed the immune response was comparable to that for the BCL1 IgM antibody in CFA (FIG. 11). This was in contrast to antisera derived from mice immunised with pSV2-B1.8 which bound only weakly to the BCL1 lymphoma (FIG. 11).

Example 3

Construction of a Vector Suitable for Use in Human Recipients

Vector Construction

The initial vectors used in example 2 above were based on Moloney Murine Leukaemia virus vectors and contained large stretches of unmodified viral sequences (Russell et al., 1993 Nucl. Acids Res. 21, 1081–1085). These vectors were shown to be effective in raising anti-idiotype responses and gave no untoward effects in the mice inoculated. Although there is no evidence of danger to man from such vectors it was decided to modify the vectors to avoid any potential risks. There was some concern about two features of the original vectors: the retroviral envelope gene (as it could theoretically be recombined into another retrovirus thus changing its tropism) and the packaging signal (which might allow packaging of the injected DNA into existing human retroviruses). Whilst changing the vector it was decided to incorporate changes which improve the vectors for use in man:—the promoter used to drive expression of the idiotypic scFv was changed to the Rous Sarcoma Virus (RSV) promoter as that has been shown to give expression when directly injected into non-human primate muscle (Jiao et al., 1992 Hum. Gene Ther. 3, 21–33). The present inventors also used a vector which contains a bacterial single strand origin of replication to allow the production of ssDNA which will facilitate sequencing the scFv portion (which is specific for that individual patient) of the vector before injecting into the patient. The vector used is based on a commercially available vector pRc/RSV (British Biotechnology/Invitrogen).

To convert this vector backbone into a vector suitable for genetic immunisation it was desirable to introduce leader sequences, termination signals and to allow for the production of fusion proteins. Fusion proteins do not appear to be necessary for the production of anti-idiotype responses but one way of enhancing the immune response might be to attach suitable proteins perhaps foreign proteins or perhaps cytokines (Tao & Levy, 1993 Nature. 362, 755–758). As fusion proteins were not necessary in animal models the initial human trial will use only a short peptide tag but this is one area for potential future modifications to the protocol.

The vector pSfi/Not.Tag1 was modified to replace the pelB leader with the human immunoglobulin VH1 leader sequence which permits the encoding of an SfiI cloning site without modification of the amino-acid sequence. This was introduced with oligonucleotides using the HindIII/PstI cloning sites and confirmed by sequencing.

This was then cloned as an EcoRI/Blunt-HindIII fragment into the NotI/Blunt-HindIII cut vector pRc/RSV to give the sequence (Seq ID No.56) between the HindIII/XbaI sites as shown in FIG. 5. The scFv for an individual patient can be inserted at the sites shown by the symbol ^.

The vector was then tested in two ways:

(i) The scFv B1.8 was cloned into the vector and then the resultant construct transfected into two cell lines—NSO (a myeloma cell line) and NIH 3T3 (a fibroblast cell line). Utilising the neomycin resistance gene in pRc/RSV stable transfectants were isolated and the supernatant assayed for scFv B1.8 antigen binding activity. In both cases the antibody fragment was expressed and bound to the hapten NIP—the antigen recognised by the monoclonal antibody B1.8. Clones were isolated from the NSO transfected cells and shown to produce 1–3 mg/L of functional scFv in spent culture supernatant.

Figure 6:
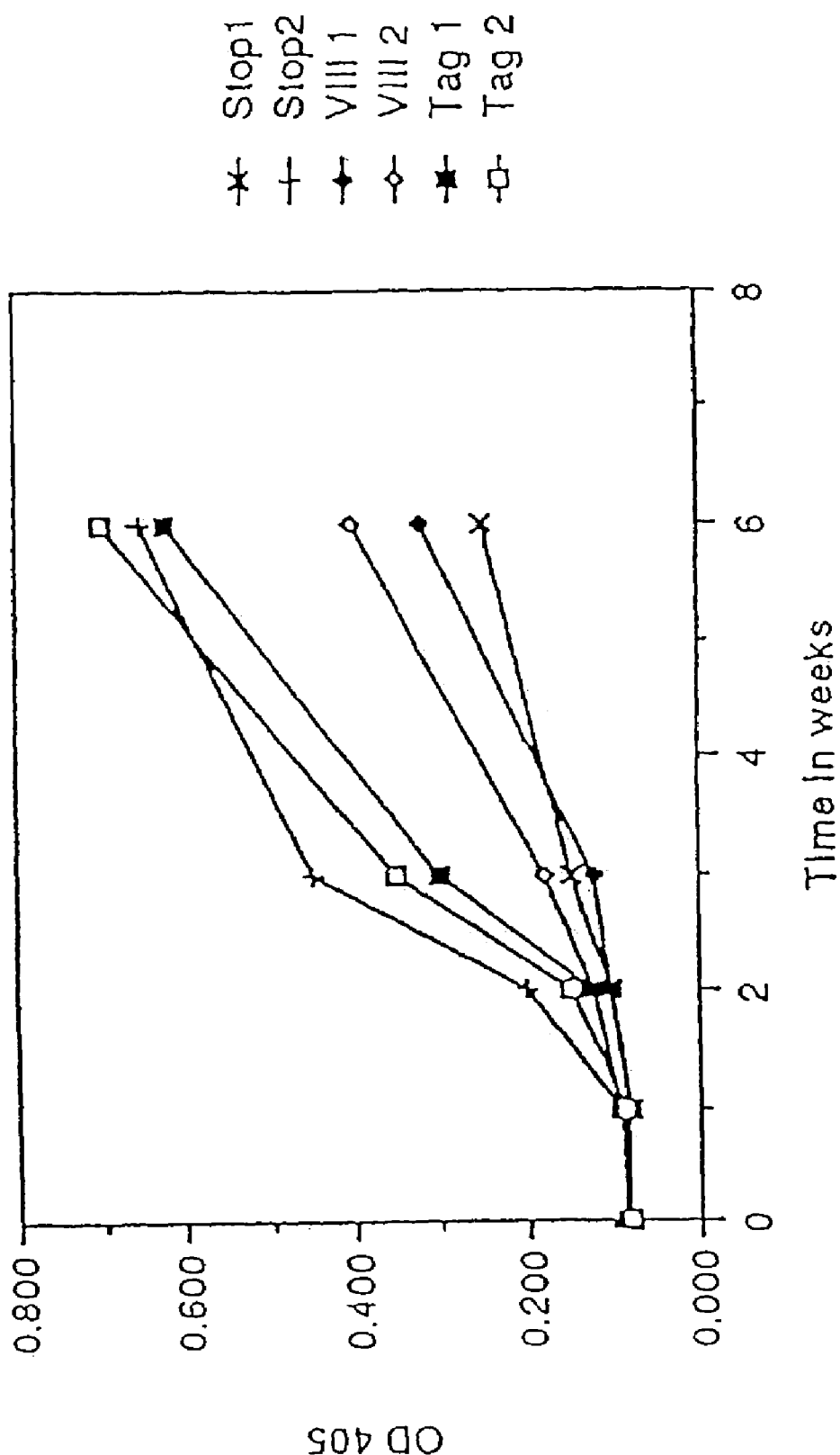
FIG. 6 is a graph showing the results of an immunisation experiment described in example 3.

(ii) The plasmid was used in a genetic immunisation experiment and compared to pSV2-B1.8. They gave comparable results and appear to be superior to a further vector which encodes the Fd bacteriophage gene 8 protein between the NotI and XbaI site (FIG. 6). The likely explanation is that in transfection experiments the level of expression was 10–100 fold lower for the scFv B1.8-Gene 8 fusion. Other investigators have found a strong correlation of level of expression and immune response when using genetic immunisation to raise immune responses to viral proteins (G. Rhodes, personal communication).

FIG. 6 (Immunisation of mice with vectors utilising the RSV promoter) shows the results of idiotypic immunisation against the scFv B1.8. The response for individual mice as determined by ELISA at 1:100 serum dilution are shown. The mice were immunised intra muscularly at weeks 0, 1, 2. Note one mouse with the stop vector (pSV2-B1.8) had a poor response and the response of mice immunised with the gene 8 fusion vector were poor (VIII 1 and VIII 2) whereas both those with the peptide tag vector gave good responses (Tag1 and Tag2).

Figure 8:
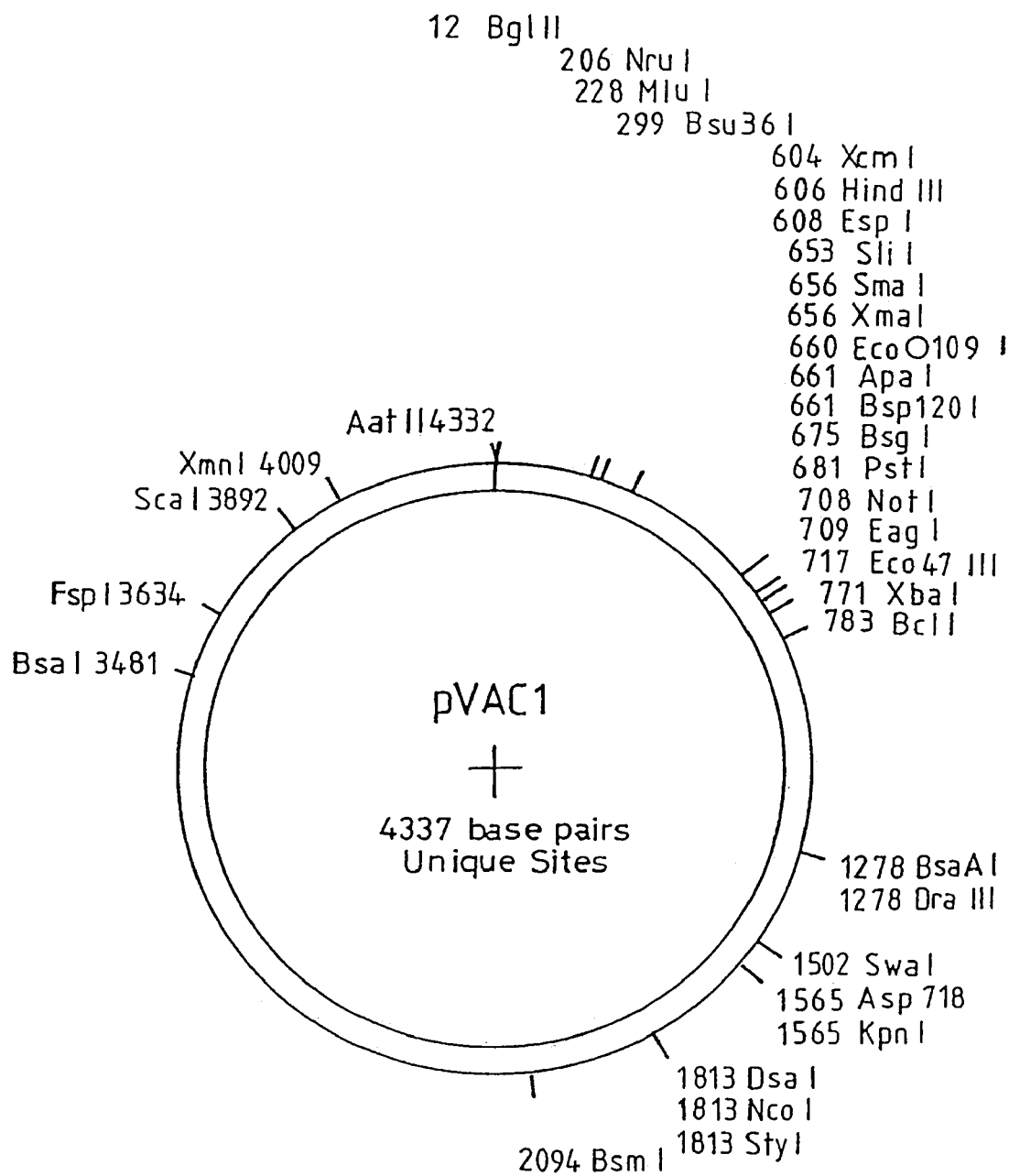
FIG. 8 shows a pVAC1 restriction map.

The sequence (Seq ID No.58) of the final vector pVAC1 is given in FIG. 7 together with a map of the unique restriction sites (FIG. 8). The sequence in lower case letters in FIG. 7 corresponds to the sequence shown in FIG. 5 through to the two stop codons, The vector pVAC1 is available from the present inventors (at the Cambridge Centre for Protein Engineering, Cambridge, United Kingdom).

Figure 9:
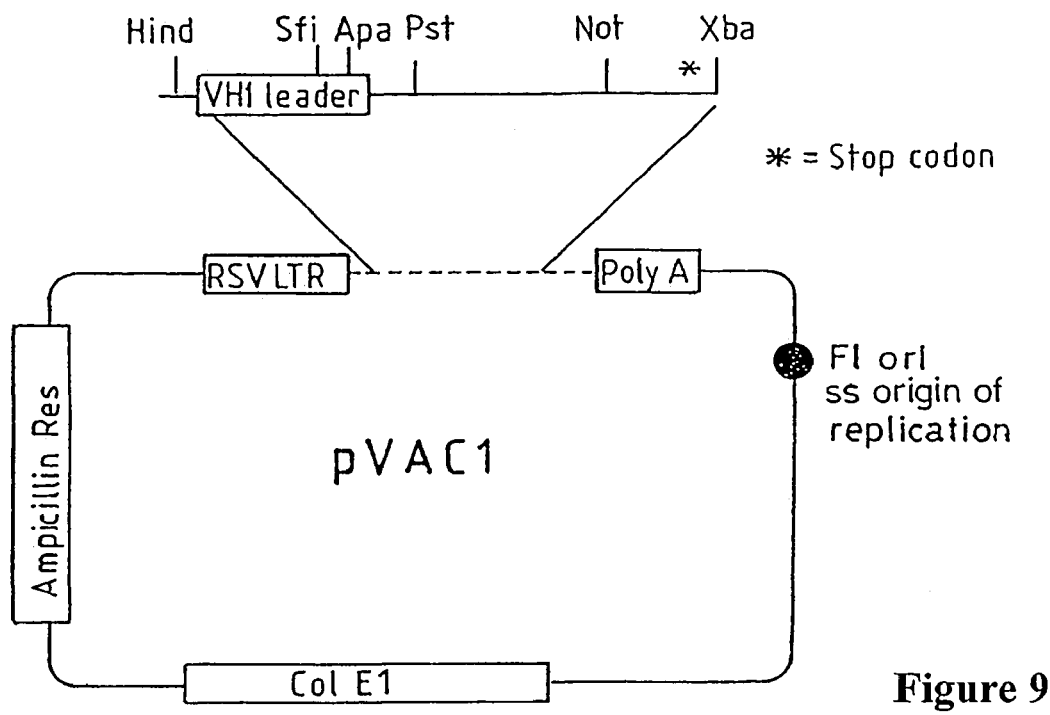
FIG. 9 shows a schematic representation of the main features of pVAC1.

FIG. 9 shows a diagrammatic representation of the vector pVAC1 indicating important restriction sites and important genes.

Figure 10:
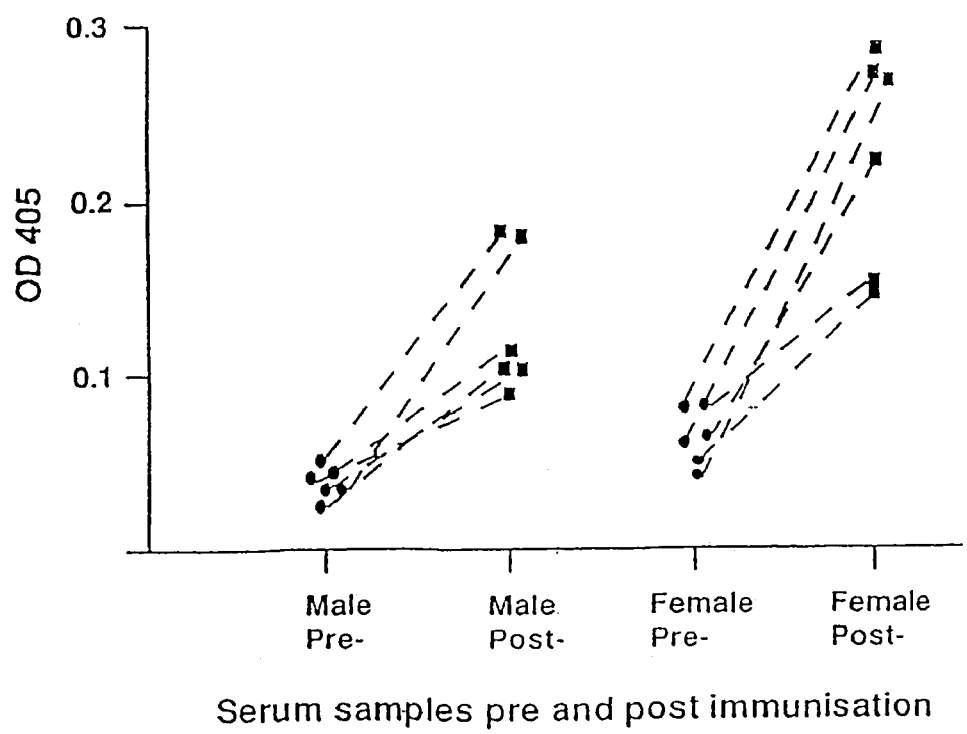
FIG. 10 is a graph showing the results of an immunisation experiment described in example 3.

FIG. 10 is a graph of O.D. (405 nm) against time for male and female mice immunised (by direct injection of DNA) with the pVAC vector expressing B1.8scFv (pVAC1.B1–8). The graph shows that, for individual mice, there was a clear increase in titre following immunisation.

Although the neomycin resistance gene is useful for in vitro testing it is unnecessary for human immunisation. The SV40 promoter used to drive the neomycin resistance gene is also associated with the same risks as other strong promoters. The plasmid to be used for human trials thus has the neomycin gene deleted by an SfiI/Bst BI digest and then blunt ligation. This prevents any such risk.

Discussion of Examples 1–3

The present inventors have demonstrated that a plasmid vaccine encoding a single chain murine antibody/retroviral envelope fusion protein induces a strong humoral immune response to the antibody moiety in BALB/c mice, whereas vaccination with the purified scFv protein mixed with Complete Freunds Adjuvant gives no detectable response. Induction of B-cell memory appears to occur as boosting with either soluble protein or a soluble scFv expression vector was effective at producing a rapid rise in antibody titre.

The humoral anti-B1.8 response to the plasmid vaccine pNIPenv was clearly superior to that raised against purified B1.8 scFv protein mixed with Complete Freunds Adjuvant. The approach disclosed herein has several advantages. Following gene transfer, there is likely to be a continuous supply of the target antigen, diminishing over a period of days or weeks, whereas injected protein may have a very short half-life. This prolonged exposure to newly synthesised antigen may be important for an optimal immune response and this argument has been used to explain the superiority of live compared to killed viral vaccines.

Antigen-specific T helper cells can amplify both humoral and cellular immune responses by direct cell interaction and by providing appropriate stimulatory cytokines. Several mechanisms can be envisaged whereby the plasmid vaccine may recruit helper T cells more efficiently.

Regardless of the mechanisms involved, the vaccination strategy employed in this study gave a strong humoral immune response to a weakly immunogenic single chain antibody fragment and was superior to vaccination with purified protein plus adjuvant. The scFv gene used in this study could be replaced with a variety of genes or gene fragments encoding other weakly immunogenic idiotypic determinants.

Episomal vectors such as those based on EBV or papova virus may have advantages over current vectors. These should allow high copy number episomal replication and may be more effective. New vectors utilising the pVAC1 HindIII/Xba1 insert have been constructed with the expression plasmid pCEP4 (Invitrogen) which contains the EBV origin of replication and BBNA. These have given enhanced levels of expression and greater stability of expression in cell culture experiments using the human osteosarcoma line 791T and may be more efficient in vivo although they also raise new safety issues for human use. More efficient methods of transfection such as liposome mediated and receptor mediated delivery may also improve the efficiency of the process.

Example 4

CD4+ T Cell Mediated Immunity Against B Cell Malignancies

ScFvPVXCP Construct Assembly and Characterisation

FIG. 12 illustrates the assembly of scFv-PVXCP fusions. The scFv from A31 lymphoma and 5T33 myeloma as well as A31FrC were assembled and cloned into pcDNA3 previously (King C. A. et al, *Nature Medicine,* 4 1281–1286 1998). ScFvs were fused in frame to the fourth codon of PVXCP (isolate CP4) via four amino-acid linker the same as in scFv fused to fragment C (King et al, 1998). PVXCP cDNA was kindly provided by Dr. K. Kanyuka (Long Ashton, LACR, Somerset, and U.K.) A31PVXCP and 5T33PVXCP fusion genes were made by two-step PCT as previously described (Spellerberg, 1997) using HF polymerase Kit (Clontech, Basingstoke, U.K.). To assemble A31PVX gene primers were as following: for the first step to amplify A31 gene 5' taatacgactcactatagggagae 3' (referred to as T7), was forward and 5' ggctggaggtccgggtccacgtttgatctccacctt 3' was reverse and to amplify PVXCP gene 5' aaacgtggacccggacctccagccaacaccactcaagct 3' forward and 5' accgcggccgctagttatggtgggggtagtgaa 3' reverse. T7 primer was corresponded to sequences derived from pcDNA3 plasmid. For the second step T7 was used as a forward primer and a reverse primer for PVXCP gene assembly was used as reverse.

To assemble 5T33PVXCP gene in the first step for the 5T33 gene T7 was also used as a forward primer and 5' ggctggaggtccgggtcctttgatttccagcttggt 3' as reverse; for the PVXCP gene 5' atcaaaggacccggacctccagccaacaccactcaagct 3' was used as a forward primer, the reverse primer was the same as for A31PVXCP gene assembly. For PVXCP (further referred to as PVXCP alone) alone gene construct 5' ccgaagcttgcaccatgaagttgtggctgaactggattttccttgtaacacttttaa atggtatccagtgtccagccaacaccactcaagct 3' was a forward primer and the reversed primer was as for the fusion constructs. The forward primer contained an Ig leader sequences, the same as in A31 scFv. Assembled constructs were cloned into pcDNA3 (invitroGen BV, Leek, Netherlands) plasmid using HindIII and NotI restriction sites. The expression of the assembled constructs was checked by TNT (Promega) and by transfection of the plasmids into COS-1 cells.

Supernatants were assayed for PVXCP by ELISA using a polyclonal anti-PVX IgG coating antibody and an alkaline phosphatase-conjugated polyclonal anti-PVX IgG detecting antibody, according to manufacturer's instructions (Bioreba, Peterborough, U.K.). All PVXCP-containing constructs produced detectable protein in the supernatants, whereas constructs containing scFv alone were negative. SDS-PAGE with Western blotting was carried out, and probed with antiserum derived from p.scFv5T33-PVXCP vaccinated mice in 1/100 dilution with a subsequent incubation with anti-mouse-HRP conjugate (Binding Site, Birmingham, UK) and developing using ECL plus reagent.

Vaccination and tumor challenge Mice were vaccinated at 6–10 weeks of age with 50 μg of plasmid DNA in saline in two sites in the quadriceps muscles, on days 0, 21 and 42, unless indicated otherwise. The A31 lymphoma was passaged as described previously (King, C. A. et al. *Nat. Med.* 4, 1281–1286. 1998). The 5T33 myeloma was passaged in C57BL/KaLwRij mice by intravenous injection. Challenge was on day 63 by intravenous injection with $10^4$ 5T33 cells or with $5\times10^4$ A31 cells.

Depletion experiments Mice were vaccinated 3 times with p.scFv5T33-PVXCP or p.scFvA31-PVXCP as described above. On day 56 mice were bled and the sera were assayed for the presence of anti-5T33 or anti-A31 antibody. On day −7, −4, −1 before challenge and on day +2, +5 mice received intraperitoneal injection of 100 μg of either anti-CD4 (YTS 191.1.2) or anti-CD8 antibody (YTS169.4.2.1) (Cobbold, S. P., Jayasuriya, A., Nash, A., Prospero T. D. and Waldmann, H. Therapy with monoclonal antibodies by elimination of T-cell subsets in vivo. *Nature* 312 548–551 1984), or normal rat IgG as a control. On day −1 before or day +6 after challenge, peripheral blood mononuclear cells were collected and double-stained with anti-CD4/anti-CD3 or anti-CD8/anti-CD3 to assess depletion and analysed by fluorescence-activated cell sorting. It was also checked that none of the depleting antibodies affected the behaviour of the tumours.

Animals were observed for survival.

Antibody responses Anti-idiotypic antibody levels in serum against IgM from the A31 lymphoma or IgG from the 5T33 myeloma were measured by ELISA as described (King C. A. et al, *Nature Medicine,* 4 1281–1286 1998). For anti-PVXCP antibody, PVXCP isolated from CsCl gradient purified virions (kindly provided by Dr. S. M. Angel) using the LiCl method of Goodman et al. (Goodman, R. M., Horne, R. W. and Hobart, J. M. Reconstitution of potato virus X in vitro. *Virology* 68 299–308 1975) was coated at 10 μg/ml, using the same ELISA conditions. Measurement of IgG1 and IgG2a subclasses in mouse serum antibodies was as described (King C. A. et al, *Nature Medicine,* 4 1281–1286 1998). To assay sera from normal human individuals for anti-PVXCP antibody, a similar ELISA was used, with goat anti-human IgG antibody conjugated to horseradish peroxidase (HRP) (Sigma, Poole, UK) at 1:2000 dilution for detection.

Electron microscopy Immunosorbent electron microscopy was used with grids coated with anti-PVX IgG (Bioreba). The grids were then negatively stained with 1% (w/v) uranyl acetate and examined using a JEOL 1200× microscope.

Figure 13:
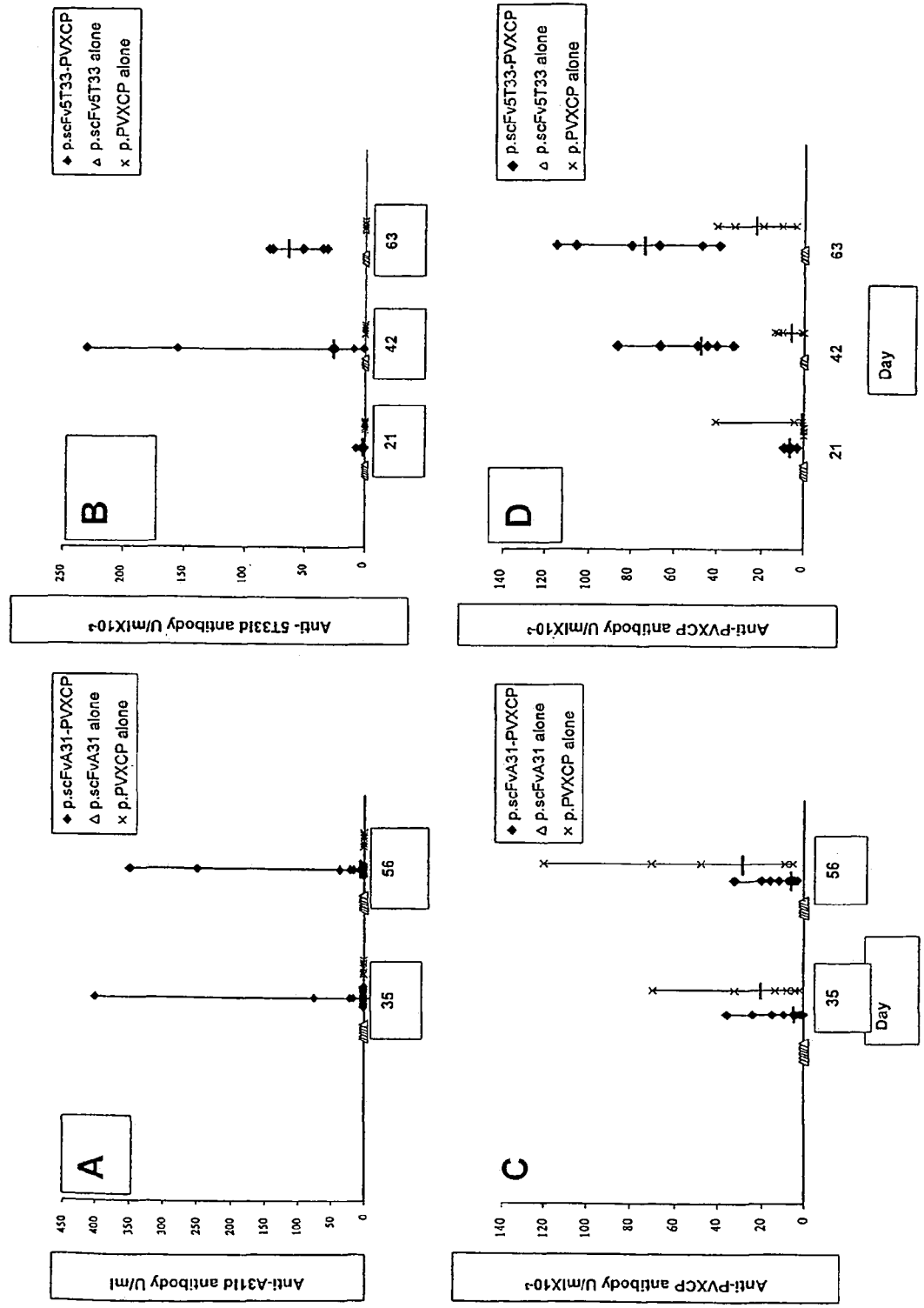
FIGS. 13A–D show graphs illustrating the levels of antibody produced in an experiment described in example 4.

Vaccination with the DNA fusion construct (scFv-PVXCP) promotes anti-Id antibody production in lymphoma (A31) and myeloma (5T33) models. The constructs containing scFv from the mouse lymphoma (A31) or myeloma (5T33) were tested in syngeneic mice either alone (p.scFv) or fused to PVXCP sequence (p.scFv-PVXCP). In each case, scFv sequence alone failed to induce significant levels of anti-Id able to recognize whole immunoglobulin (FIGS. 13 (A) (B)). However, the scFv-PVXCP fusion genes induced anti-Id antibody in both models (A) (B). Levels were variable, with only 30–50% of mice responding in the A31 lymphoma model, and 90–100% in the 5T33 model. These results were similar in repeated experiments. As expected, the control plasmid containing PVXCP sequence alone did not induce anti-Id antibody. Constructs containing PVXCP sequence either alone, or in fusion, induced antibodies against PVXCP (FIGS. 13(C) (D)), with the p.scFv5T33-PVXCP fusion consistently being most efficient (D), possibly due to a higher level of expression. For all responses, there was an increase in antibody following the second injection on day 21, and a further smaller rise following the third injection on day 42. Analysis of pooled sera for immunoglobulin subclasses of antibodies against either scFv or PVXCP showed dominance of IgG2a, with only very low levels of IgG1. In the A31 model, IgG1 could not be detected, and in the 5T33 model, the ratios of IgG1:IgG2a for anti-Id or anti-PVXCP were 0.08:1 and 0.02:1, respectively.

DNA Fusion Constructs Induce Protective Immunity Against Lymphoma and Myeloma

Figure 14:
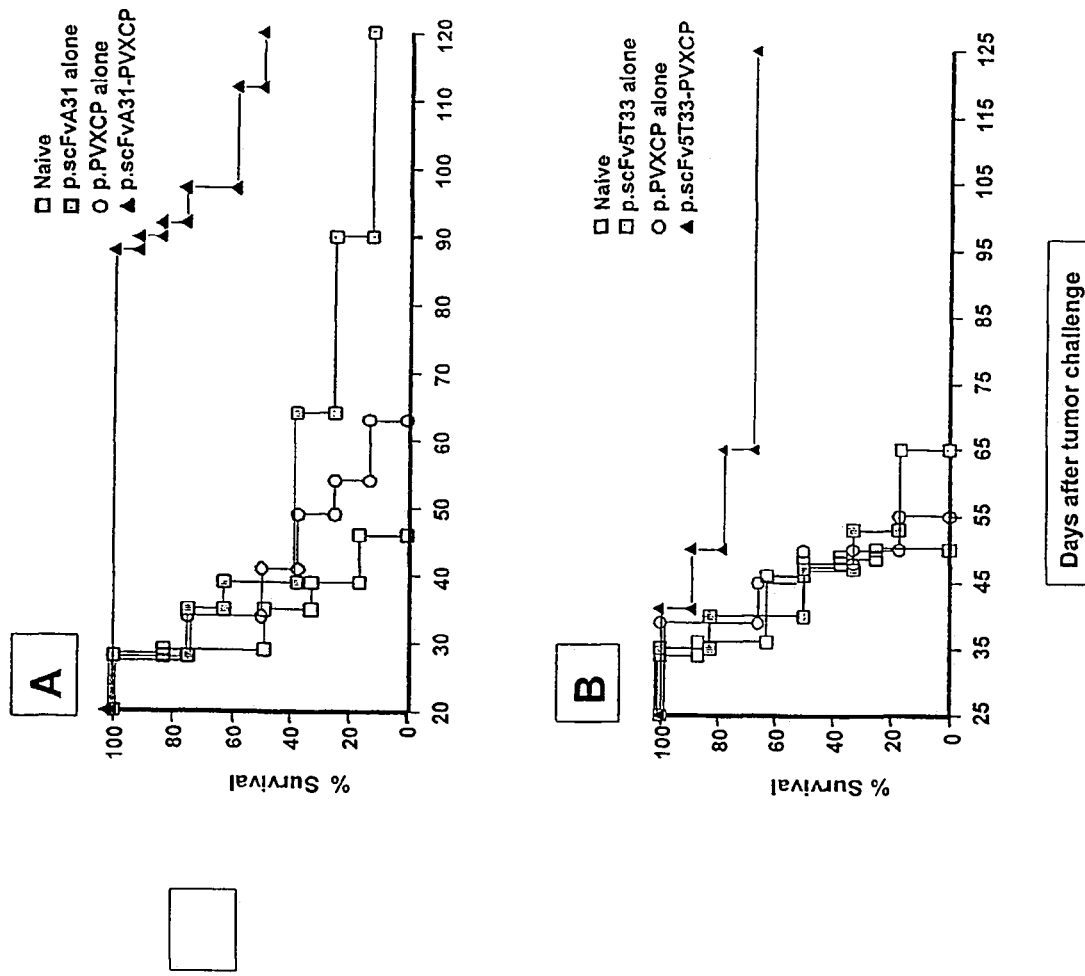
FIGS. 14A and B show graphs illustrating the protection against challenge with the A31 lymphoma or the 5T33 myeloma following DNA vaccination.
Figure 15:
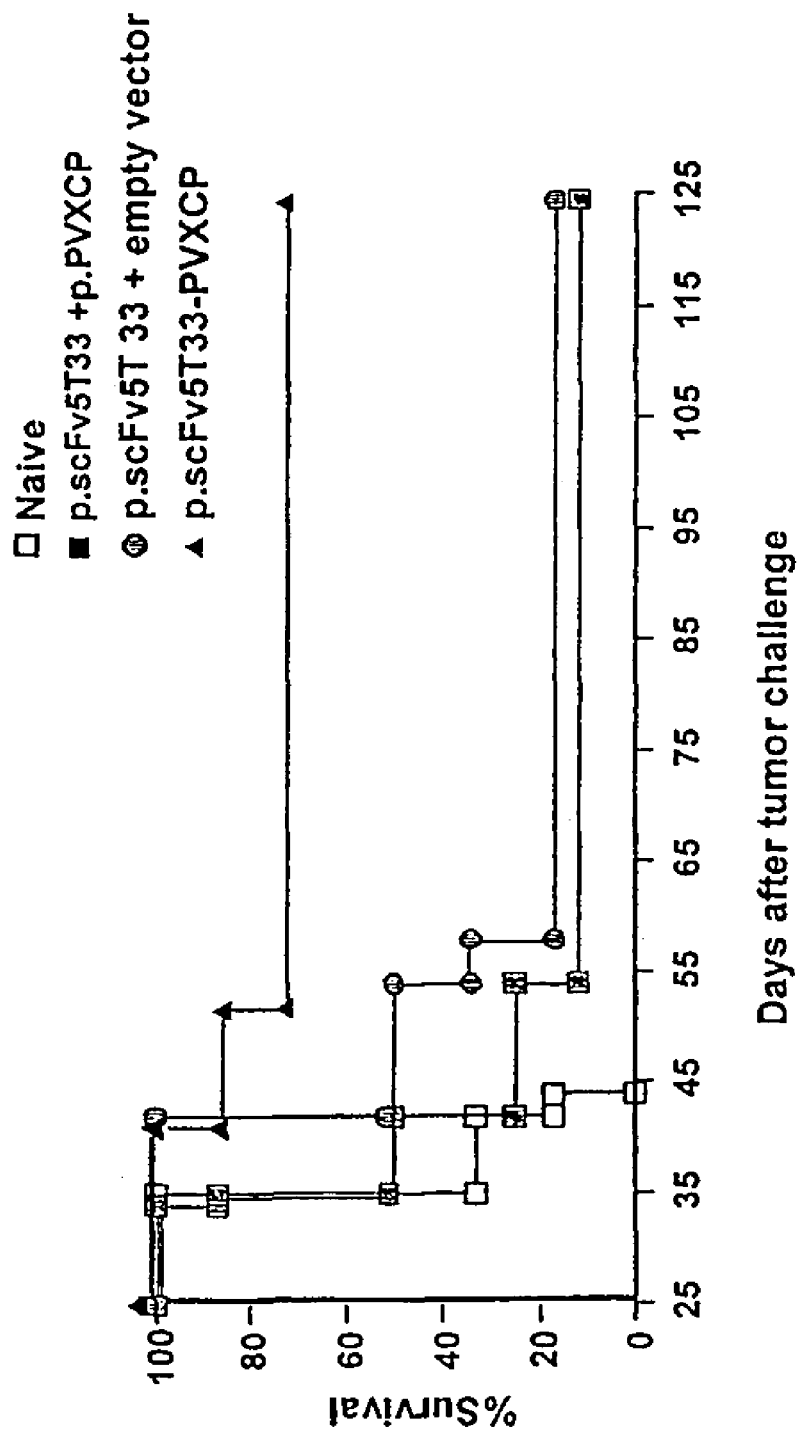
FIG. 15 shows a graph illustrating protection against challenge with 5T33 myeloma following vaccination with fused and separate DNA sequences.
Figure 16:
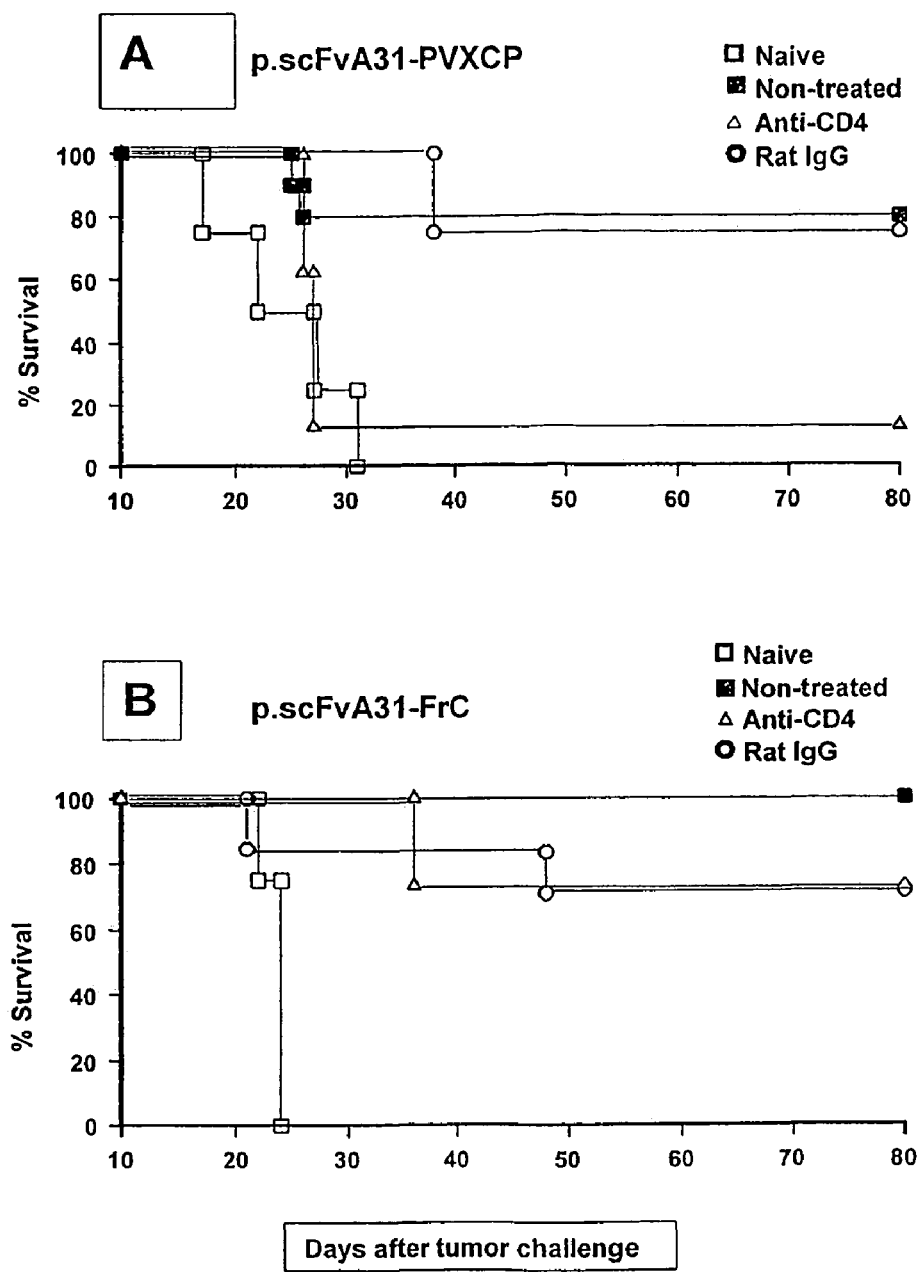
FIGS. 16A and B show graphs illustrating protection against challenge with A31 lymphoma in mice treated or untreated with anti-CD4+monoclonal antibodies after vaccination.

Vaccination of syngeneic mice with the p.scFv-PVXCP fusion constructs induced protective immunity against both lymphoma (A31) and myeloma (5T33) (FIGS. 14A and 16B). In each case, p.scFv alone was ineffective, and the p.PVXCP control was negative. For the lymphoma, in which anti-Id antibodies were detected in only ~50% of mice, all showed evidence for protection, indicating a requirement for very little or no antibody. Protection experiments have been repeated three times with similar results. In the A31 model, some mice developed lymphoma at a late stage (>90 days), but there was no clear correlation between long-term survival and antibody levels at challenge. Further investigation is required to assess the mechanism of escape at this late stage. In both models, injection of separate plasmids encoding scFv or PVXCP failed to induce protection, demonstrating a requirement for fusion (data shown for the 5T33 model in FIG. 15).

Protection Against and Myeloma Involves CD4+ T Cells

Figure 17:
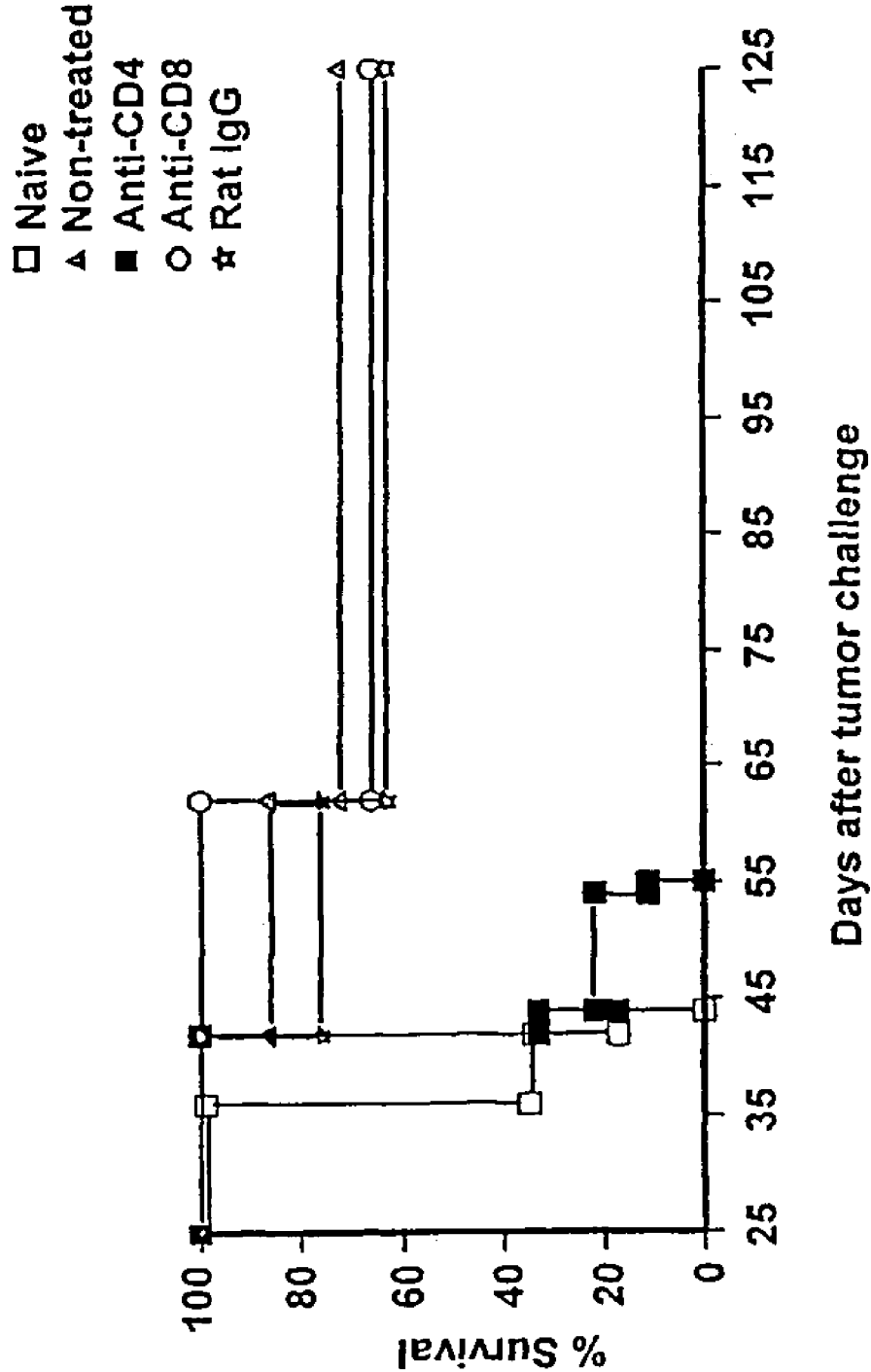
FIG. 17 show a graph illustrating protection against challenge with 5T33 myeloma in mice treated or untreated with anti-CD4+ monoclonal antibodies after vaccination.
Figure 19:
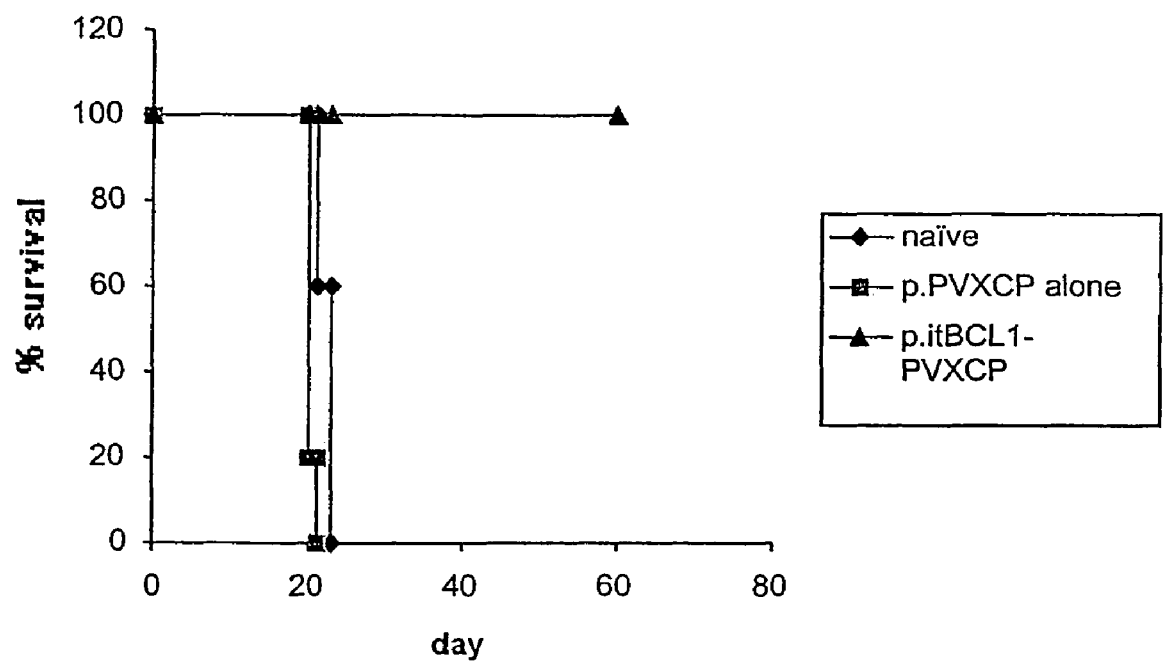
FIG. 19 shows the results of an experiment described in example 5. The graph shows protection after vaccination with p.scFvBCL1-PVXCP (3×vaccinated then challenge with $5 \times 10^4$ BCL1 cells).

For the A31 lymphoma, depletion of CD4+ T cells postvaccination, by repeated injection of the anti-CD4 monoclonal antibody (mAb), completely abrogated protection (FIG. 16A). This contrasts with results using a construct containing scFv sequence fused to a sequence encoding the Fragment C of tetanus toxin (scFv-FrC). As reported previously (King C. A. et al, Nature Medicine, 4 1281–1286 1998), and confirmed in FIG. 16B, this construct induces protection against the A31 lymphoma. However, this protection is not abrogated by depletion of CD4+ T cells (FIG. 16B), and is therefore probably depends on antibody. It appears that antibody may be less critical for the protection induced by scFv-PVXCP. In the myeloma model, protection induced by the scFv-PVXCP construct was again abrogated by depletion of CD4+ T cells (FIG. 17). This result is consistent with the ineffectiveness of anti-Id antibody in protection against a surface Ig-ve tumor, and with the involvement of a cellular mechanism. There was no effect on protection against myeloma when CD8+ T cells were depleted (FIG. 17). The role of CD8+ T cells in protection against the A31 lymphoma was more difficult to evaluate since, in contrast to 5T33, depletion had some effect on the growth of the A31 tumor.

ScFv-PVXCP fusion protein forms self aggregating particles To investigate the molecular nature of the expressed scFv-PVXCP fusion protein, constructs were transfected into Cos-1 cells and supernatants collected. The fusion protein from the 5T33 myeloma was expressed at the highest level (~50 ng/ml), and this was therefore selected for further investigation. Using ELISA to detect PVXCP protein, we found that centrifugation at 40,000 rpm (135,000×g) for 2 hours sedimented all detectable PVXCP reactivity, indicating that the fusion protein was of large molecular size. A similar result was obtained using plant-derived PVXCP alone. Since the fusion protein or the free PVXCP could be resolved by SDS-PAGE to monomers of the expected sizes of 54 KD or 24 KD respectively (FIG. 18A), the expressed proteins must be undergoing self aggregation, presumably mediated by the PVXCP component. The supernatants containing expressed scFv-PVXCP or PVXCP proteins were examined by electron microscopy using immunotrapping with anti-PVX IgG. Aggregates were detectable (FIG. 18B) with an appearance was similar to that of PVXCP isolated from virus particles, reflecting the well-documented tendency of Potexvirus coat proteins to self-aggregate. Under physiological conditions, PVXCP forms aggregates comprising two-layer disks with 9 subunits per layer, and stacks thereof (Goodman, R. M., Horne, R. W. and Hobart, J. M. Reconstitution of potato virus X in vitro. *Virology* 68 299–308 1975, Erikson, J. W., Bancroft, J. B. and Stillman, M. J. Circular dichroism studies of papaya mosaic virus coat protein and its polymers. *J. Mol. Biol.* 147 337–349 1981). It appears that fusion of scFv does not change the shape or size of the aggregates, and that the scFv fused to PVXCP will present multiple copies on the PVXCP aggregates. As expected, under the conditions of expression, in the absence of viral RNA, the PVX CP subunits do not form virus-like helices.

Discussion of Example 4

DNA constructs provide a platform for manipulation of tumor-derived genes, with the aim of optimising presentation of the encoded antigen to the immune system (Gurunathan, S., Klinman, D. M. & Seder, R. A. DNA vaccines: immunology, application, and optimization. *Annu. Rev. Immunol.* 18, 927–974 2000). For cancer, DNA vaccines allow rapid testing of the ability of chosen sequences to induce effector mechanisms able to suppress tumor growth in model systems. For idiotypic antigens of B-cell tumors, it was already clear that simple constructs containing scFv only were unable to induce significant anti-Id responses (Stevenson, F. K. et al. Idiotypic DNA vaccines against B-cell lymphoma. *Immunol. Rev.* 145, 211–228 1995), but that fusion of the FrC sequence of tetanus toxin led to promotion of protective immunity against lymphoma and myeloma (King C. A. et al, *Nature Medicine*, 4 1281–1286 1998). However, the majority of patients will have pre-existing immunity against tetanus toxin, and, although this does not appear to prevent induction of immunity against the scFv-FrC fusion gene (King C. A. et al, *Nature Medicine,* 4 1281-1286 1998), it could affect the pathways induced. The inventors therefore chose to investigate an alternative promotional gene, derived from a plant viral coat protein (PVXCP). In contrast to FrC, no antibody against PVXCP was detected in human sera (data not shown). Therefore, there would be no pre-existing antibody at the priming stage, although such antibody would develop after vaccination. However, independently of the fact that this is a primary antigen in humans, the inventors have found that the scFv-PVXCP fusion gene generates a distinct CD4+ T-cell mediated protective mechanism against B-cell tumours.

The requirement for fusion of the scFv and PVXCP proteins to promote a specific T-cell response appears to be an example of "linked T-cell help". This phenomenon, in which an immunologically silent determinant can be rendered immunogenic if linked to a dominant pathogen-derived antigen has been described for a mucin (MUC-1) peptide linked to a parasite-derived peptide, delivered within a whole Ig molecule (Gerloni, M. et al. Functional cooperation between T helper cell determinants. *Proc. Natl. Acad. Sci. USA* 97, 13269–13274 2000). Although in that model both epitopes were foreign, and tumor protection was not assessed, activation of the CD4+ T cells by linkage was clearly demonstrated, with the mechanism likely to involve up-regulation of the costimulatory ability of antigen-presenting cells (Gerloni, M. et al. Functional cooperation between T helper cell determinants. *Proc. Natl. Acad. Sci. USA* 97, 13269–13274 2000). Here, the inventors have shown that CD4+ T cells against a linked autologous tumor antigen can also be promoted by this mechanism. The CD4+ T-cell population appears able to protect against lymphoma, and is clearly critical for protection against surface Ig-ve myeloma.

One feature of the expressed scFv-PVXCP fusion protein is that it forms aggregates, including stacked-disk structures (Goodman, R. M., Horne, R. W. & Hobart, J. M. Reconstitution of potato virus X in vitro. *Virology* 68, 299–308 1975). Activation of the immune response is known to be influenced by the molecular form of the antigen, with large aggregates being particularly immunogenic, presumably because pathogens commonly have this structure (Zinkernagel, R. M. Immunology and autoimmunity studied with viruses. in *The molecular basis of cellular defence mechanisms* 105–129 Wiley, Chichester, 1997). For DNA vaccines, it is not yet known whether the major route of presentation in vivo involves export from transfected muscle cells (Ulmer, J. B., Deck, R. R., DeWitt, C. M., Donnely, J. J. & Liu, M. A. Generation of MHC class I-restricted cytotoxic T lymphocytes by expression of a viral protein in muscle cells: antigen presentation by non-muscle cells. *Immunology* 89, 59–67 1996, Corr, M., von Damm, A., Lee, D. L. & Tighe, H. In vivo priming by DNA occurs predominantly by antigene transfer. *J. Immunol.* 163, 4721–4727 1999) or direct presentation by transfected APCs (Condon, C., Watkins, S. C., Celluzzi, C. M., Thompson, K. & Falo, L. D., Jr. DNA-based immunization by in vivo transfection of dendritic cells. *Nat. Med.* 2, 1122–1128 1996, Casares, S., Inaba, K., Brumeanu, T. D., Steinman, R. M. & Bona, C. A. Antigen presentation by dendritic cells after immunization with DNA encoding a major histocompatibily complex class II-restricted viral epitope. *J. Exp. Med.* 186, 1481–1486 1997). All the constructs incorporate a leader sequence, and fusion proteins can be exported from COS-1 cells. However, fusion of PVXCP gives rise to a different immune outcome as compared to Fragment C of tetanus toxin. For scFv-PVXCP, the anti-Id antibody response is almost entirely of the IgG2a subclass, whereas fusion of scFv-FrC induces a high level of IgG1 (King C. A. et al, *Nature Medicine,* 4 1281–1286 1998). In the 5T33 model, PVXCP fusion induced anti-Id with an IgG1:IgG2a ratio of 0.08:1, dramatically contrasting with the ratio of 28:1 induced by scFv-FrC (King C. A. et al, *Nature Medicine,* 4 1281–1286 1998). This suggests that the aggregated antigen amplifies the $T_H1$-dominated response already activated by the cytokine environment generated by injection of DNA (Roman, M. et al. Immunostimulatory DNA sequences function as T helper-1-promiting adjuvants. *Nat. Med.* 3, 849–854 1997). Induction of an IgG2a-dominant response has also been noted using peptides linked to chimeric virus particles (McInerney, T. L., Brennan, F. R., Jones, T. D. & Dimmock, N. J. Analysis of the ability of five adjuvants to enhance immmuhe responses to a chimeric plant virus displaying an HIV-1 peptide. *Vaccine* 17, 1359–1368 1999). The principles of amplification of immune responses against tumor antigens by genetic linkage may be widely applicable. For DNA vaccines, the inventors have already shown that promotion of antibody responses against several tumour antigens, including MUC-1 and carcinoembryonic antigen, can be achieved by fusion with FrC 30. Stevenson, F. K. et al. Genetic vaccination against defined tumour antigens of B-cell malignancies. *Rev. Clin. Exp. Hematol.* 9 2–21 1999). It appears that PVXCP may be superior in amplifying CD4+ T cell responses against linked tumor antigens, and these are being tested. Promotion of CD8+ T-cell responses may also occur via linkage, and although the murine scFv sequences contain few or no candidate MHC Class I-binding peptides (Zhu, D. et al. Immunoglobulin $V_H$ gene sequence analysis of spontaneous murine immunoglobulin-secreting B-cell tumours with clinical features of human disease. *Immunology* 93, 162–170 1998), these can be found in other tumour antigens. It is clear that there are many effector pathways that could act against cancer cells, and that fusion genes can be selected to activate those most appropriate for the target antigen.

In summary, the present inventors have genetically fused PVXCP to a lymphoma-associated antigen (scFv-A31) and used the construct for DNA vaccination of mice. This led to elevated antibody responses and protection against challenge with A31 lymphoma. Moreover, the inventors have shown that this protection was mediated by CD4 positive cells. This is in contrast with DNA vaccination using fusion of FrC to scFv-A31, where such protection is mediated only by antibody to scFv. The inventors have also fused a myeloma-specific antigen scFv-5T33 to PVXCP with subsequent vaccination of mice with the construct. This resulted in induction of antibody response against scFv-5T33 and protection against challenge with 5T33 myeloma. The inventors have also determined that such protection against myeloma was mediated by CD4 positive T cells. This depletion was achieved by using anti-CD4+ antibodies to remove cells prior to challenge by the tumour.

The inventors have concluded that plant viral coat proteins, e.g. PVXCP, can act as an adjuvant sequence for induction of protective immunity against at least lymphoma and myeloma. They have further noted that there is some distinction between PVXCP and FrC, both in terms of molecular structure and in terms of the pathways of immunity induced via DNA vaccination.

Example 5

Immunogenic Properties of PVXCP-Fusion Vaccine in BCL1 Lymphoma Model

The inventors evaluated the immunogenic properties of PVXCP-based DNA vaccines in another, BCL1 lymphoma model, which is similar to the A31 lymphoma model of example 4 and also displays a tumour-specific immunoglobulin on the cell surface.

scFv derived from BCL1 tumour immunoglobulin was fused to PVXCP following the procedure described in example 4. Mice were vaccinated with the resulting p.scFvBCL1-PVXCP vaccine, which generated antibody responses against BCL1 immunoglobulin and protected the mice upon challenge with BCL1 tumour. The results are shown in FIG. 19.

SEQUENCE LISTING

```
<160> NUMBER OF SEQ ID NOS: 73

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9
```

000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

-continued

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43

```
<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide for amplifying MoMLV env

<400> SEQUENCE: 49
ctgcaggagc tcgagatcaa acgggcggcc gcacctcatc aagtctataa tatc        54

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide for amplifying MoMLV env

<400> SEQUENCE: 50
gccagaacgg ggtttggcc                                                19

<210> SEQ ID NO 51
<211> LENGTH: 57
<212> TYPE: DNA
<213> ORGANISM: Artificial Sequence
<220> FEATURE:
<223> OTHER INFORMATION: Description of Artificial Sequence:
      Oligonucleotide for amplifying MoMLV env

<400> SEQUENCE: 51
tttgatctcg agctcctgca gggccggctg ggccgcactg gagccgggcg aagcagt     57
```

```
<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide for amplifying MoMLV env

<400> SEQUENCE: 52
aattacattg tgcatacaga ccc                                      23

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide for amplifying MoMLV pol

<400> SEQUENCE: 53
taatcactac agatctagac tgacatggcg cgt                           33

<210> SEQ ID NO 54
<211> LENGTH: 46
<212> TYPE: DNA
<213> ORGANISM: Artificial Sequence
<220> FEATURE:
<223> OTHER INFORMATION: Description of Artificial Sequence:
      PCR primer for mutated MoMLV env

<400> SEQUENCE: 54
tactcgcggc ccaaccggcc atggcccagg tsmarctgca gsagtc             46

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence:
      PCR primer for mutated MoMLV env

<400> SEQUENCE: 55
aacagtttct gcggccgcct cctcagagga c                             31

<210> SEQ ID NO 56
<211> LENGTH: 172
<212> TYPE: DNA
<213> ORGANISM: Artificial Sequence
<220> FEATURE:
<221> NAME/KEY: CDS
<222> LOCATION: (1)..(144)
<220> FEATURE:
<223> OTHER INFORMATION: Description of Artificial Sequence: HindIII
      - XbaI fragment of the vector pVAC1

<400> SEQUENCE: 56 aag ctt agc atg gac tgg acc tgg agg gtc ttc tgc ttg ctg gct gtg    48
Lys Leu Ser Met Asp Trp Thr Trp Arg Val Phe Cys Leu Leu Ala Val
 1               5                  10                  15 gcc ccg ggg gcc cac tcc cag gtg cag ctg cag gtc gac ctc gag atc    96
Ala Pro Gly Ala His Ser Gln Val Gln Leu Gln Val Asp Leu Glu Ile
            20                  25                  30 aaa cgg gcg gcc gca agc gct tgg cgt cac ccg cag ttc ggt ggt taa   144
Lys Arg Ala Ala Ala Ser Ala Trp Arg His Pro Gln Phe Gly Gly
        35                  40                  45 taagaattgc tcgagcatgc atctagag                                    172
```

<210> SEQ ID NO 57
<211> LENGTH: 47
<212> TYPE: PRT
<213> ORGANISM: Artificial Sequence
<220> FEATURE:
<223> OTHER INFORMATION: Description of Artificial Sequence: HindIII
    - XbaI fragment of the vector pVAC1

<400> SEQUENCE: 57

Lys Leu Ser Met Asp Trp Thr Trp Arg Val Phe Cys Leu Leu Ala Val
 1               5                  10                  15

Ala Pro Gly Ala His Ser Gln Val Gln Leu Gln Val Asp Leu Glu Ile
            20                  25                  30

Lys Arg Ala Ala Ala Ser Ala Trp Arg His Pro Gln Phe Gly Gly
        35                  40                  45

<210> SEQ ID NO 58
<211> LENGTH: 4341
<212> TYPE: DNA
<213> ORGANISM: Artificial Sequence
<220> FEATURE:
<223> OTHER INFORMATION: Description of Artificial Sequence: Vector
    pVAC1

<400> SEQUENCE: 58

| | | | | | | |
|---|---|---|---|---|---|---|
| gacggatcgg | gagatctccc | gatcccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgtatctgag | 240 |
| gggactaggg | tgtgtttagg | cgaaaagcgg | ggcttcggtt | gtacgcggtt | aggagtcccc | 300 |
| tcaggatata | gtagtttcgc | ttttgcatag | ggagggggaa | atgtagtctt | atgcaataca | 360 |
| cttgtagtct | tgcaacatgg | taacgatgag | ttagcaacat | gccttacaag | gagagaaaaa | 420 |
| gcaccgtgca | tgccgattgg | tggaagtaag | gtggtacgat | cgtgccttat | taggaaggca | 480 |
| acagacaggt | ctgacatgga | ttggacgaac | cactgaattc | cgcattgcag | agataattgt | 540 |
| atttaagtgc | ctagctcgat | acaataaacg | ccatttgacc | attcaccaca | ttggtgtgca | 600 |
| cctccaagct | tagcatggac | tggacctgga | gggtcttctg | cttgctggct | gtggccccgg | 660 |
| gggcccactc | ccaggtgcag | ctgcaggtcg | acctcgagat | caaacgggcg | gccgcaagcg | 720 |
| cttggcgtca | cccgcagttc | ggtggttaat | aagaattggc | cgctcgagca | tgcatctaga | 780 |
| gctcgctgat | cagcctcgac | tgtgccttct | agttgccagc | catctgttgt | ttgcccctcc | 840 |
| cccgtgcctt | ccttgaccct | ggaaggtgcc | actcccactg | tcctttccta | ataaaatgag | 900 |
| gaaattgcat | cgcattgtct | gagtaggtgt | cattctattc | tggggggtgg | ggtggggcag | 960 |
| gacagcaagg | gggaggattg | ggaagacaat | agcaggcatg | ctggggatgc | ggtgggctct | 1020 |
| atggaaccag | ctggggctcg | aggggggatc | cccacgcgcc | ctgtagcggc | gcattaagcg | 1080 |
| cggcgggtgt | ggtggttacg | cgcagcgtga | ccgctacact | tgccagcgcc | ctagcgcccg | 1140 |
| ctcctttcgc | tttcttccct | tcctttctcg | ccacgttcgc | cggctttccc | cgtcaagctc | 1200 |
| taaatcgggg | catcccttta | gggttccgat | ttagtgcttt | acggcacctc | gaccccaaaa | 1260 |
| aacttgatta | gggtgatggt | tcacgtagtg | ggccatcgcc | ctgatagacg | gttttcgcc | 1320 |
| ctttgacgtt | ggagtccacg | ttctttaata | gtggactctt | gttccaaact | ggaacaacac | 1380 |
| tcaaccctat | ctcggtctat | tcttttgatt | tataagggat | tttgggatt | tcggcctatt | 1440 |

```
ggttaaaaaa tgagctgatt taacaaaaat ttaacgcgaa ttttaacaaa atattaacgt    1500
ttacaattta aatatttgct tatacaatct tcctgttttt ggggcttttc tgattatcaa    1560
ccggggtggg taccgagctc gaattctgtg aatgtgtgt cagttagggt gtggaaagtc     1620
cccaggctcc ccaggcaggc agaagtatgc aaagcatgca tctcaattag tcagcaacca    1680
ggtgtggaaa gtccccaggc tccccagcag gcagaagtat gcaaagcatg catctcaatt    1740
agtcagcaac catagtcccg cccctaactc cgcccatccc gcccctaact ccgcccagtt    1800
ccgcccattc tccgcccat ggctgactaa tttttttat ttatgcagag gccgaggccg      1860
cgaaatgacc gaccaagcga cgcccaacct gccatcacga gatttcgatt ccaccgccgc    1920
cttctatgaa aggttgggct tcggaatcgt tttccgggac gccggctgga tgatcctcca    1980
gcgcggggat ctcatgctgg agttcttcgc ccaccccaac ttgtttattg cagcttataa    2040
tggttacaaa taaagcaata gcatcacaaa tttcacaaat aaagcatttt tttcactgca    2100
ttctagttgt ggtttgtcca aactcatcaa tgtatcttat catgtctgga tcccgtcgac    2160
ctcgagagct tggcgtaatc atggtcatag ctgtttcctg tgtgaaattg ttatccgctc    2220
acaattccac acaacatacg agccggaagc ataaagtgta aagcctgggg tgcctaatga    2280
gtgagctaac tcacattaat tgcgttgcgc tcactgcccg ctttccagtc gggaaacctg    2340
tcgtgccagc tgcattaatg aatcggccaa cgcgcgggga gaggcggttt gcgtattggg    2400
cgctcttccg cttcctcgct cactgactcg ctgcgctcgg tcgttcggct gcggcgagcg    2460
gtatcagctc actcaaaggc ggtaatacgg ttatccacag aatcagggga taacgcagga    2520
aagaacatgt gagcaaaagg ccagcaaaag gccaggaacc gtaaaaaggc cgcgttgctg    2580
gcgtttttcc ataggctccg ccccctgac gagcatcaca aaaatcgacg ctcaagtcag     2640
aggtggcgaa acccgacagg actataaaga taccaggcgt ttccccctgg aagctccctc    2700
gtgcgctctc ctgttccgac cctgccgctt accggatacc tgtccgcctt ctcccttcg     2760
ggaagcgtgg cgctttctca atgctcacgc tgtaggtatc tcagttcggt gtaggtcgtt    2820
cgctccaagc tgggctgtgt gcacgaaccc ccgttcagc ccgaccgctg cgccttatcc     2880
ggtaactatc gtcttgagtc aacccggta agacacgact tatcgccact ggcagcagcc     2940
actggtaaca ggattagcag agcgaggtat gtaggcggtg ctacagagtt cttgaagtgg    3000
tggcctaact acggctacac tagaaggaca gtatttggta tctgcgctct gctgaagcca    3060
gttaccttcg gaaaaagagt tggtagctct tgatccggca aacaaaccac cgctggtagc    3120
ggtggttttt ttgtttgcaa gcagcagatt acgcgcagaa aaaaggatc tcaagaagat     3180
cctttgatct tttctacggg gtctgacgct cagtggaacg aaaactcacg ttaagggatt    3240
ttggtcatga gattatcaaa aaggatcttc acctagatcc ttttaaatta aaaatgaagt    3300
tttaaatcaa tctaaagtat atatgagtaa acttggtctg acagttacca atgcttaatc    3360
agtgaggcac ctatctcagc gatctgtcta tttcgttcat ccatagttgc ctgactcccc    3420
gtcgtgtaga taactacgat acgggagggc ttaccatctg gccccagtgc tgcaatgata    3480
ccgcgagacc cacgctcacc ggctccagat ttatcagcaa taaaccagcc agccggaagg    3540
gccgagcgca gaagtggtcc tgcaacttta tccgcctcca tccagtctat taattgttgc    3600
cgggaagcta gagtaagtag ttcgccagtt aatagtttgc gcaacgttgt tgccattgct    3660
acaggcatcg tggtgtcacg ctcgtcgttt ggtatggctt cattcagctc cggttcccaa    3720
cgatcaaggc gagttacatg atccccatg ttgtgcaaaa aagcggttag ctccttcggt     3780
cctccgatcg ttgtcagaag taagttggcc gcagtgttat cactcatggt tatggcagca    3840
```

```
ctgcataatt ctcttactgt catgccatcc gtaagatgct tttctgtgac tggtgagtac    3900
tcaaccaagt cattctgaga atagtgtatg cggcgaccga gttgctcttg cccggcgtca    3960
atacgggata ataccgcgcc acatagcaga actttaaaag tgctcatcat tggaaaacgt    4020 tcttcgggc gaaaactctc aaggatctta ccgctgttga gatccagttc gatgtaaccc     4080
actcgtgcac ccaactgatc ttcagcatct tttactttca ccagcgtttc tgggtgagca    4140
aaaacaggaa ggcaaaatgc cgcaaaaaag gaataaggg cgacacggaa atgttgaata     4200
ctcatactct cctttttca atattattga agcatttatc agggttattg tctcatgagc     4260
ggatacatat ttgaatgtat ttagaaaaat aaacaaatag ggttccgcg cacatttccc     4320 cgaaaagtgc cacctgacgt c                                              4341
```

<210> SEQ ID NO 59
<211> LENGTH: 190
<212> TYPE: DNA
<213> ORGANISM: Artificial Sequence
<220> FEATURE:
<221> NAME/KEY: CDS
<222> LOCATION: (35)..(181)
<220> FEATURE:
<223> OTHER INFORMATION: Description of Artificial Sequence: Vector with Myc Tag

<400> SEQUENCE: 59

```
gcatgcaaaa ttctatttca aggagacagt cata atg aaa tac cta ttg cct acg       55
                                     Met Lys Tyr Leu Leu Pro Thr
                                      1               5 gca gcc gct gga ttg tta tta ctc gcg gcc cag ccg gcc atg gcc cag        103
Ala Ala Ala Gly Leu Leu Leu Leu Ala Ala Gln Pro Ala Met Ala Gln
        10                  15                  20 gtg cag ctg cag gtc gac ctc gag atc aaa cgg gcg gcc gca gaa caa        151
Val Gln Leu Gln Val Asp Leu Glu Ile Lys Arg Ala Ala Ala Glu Gln
    25                  30                  35 aaa ctc atc tca gaa gag gat ctg aat taa taagaattc                      190
Lys Leu Ile Ser Glu Glu Asp Leu Asn
 40                  45
```

<210> SEQ ID NO 60
<211> LENGTH: 48
<212> TYPE: PRT
<213> ORGANISM: Artificial Sequence
<220> FEATURE:
<223> OTHER INFORMATION: Description of Artificial Sequence: Vector with Myc Tag

<400> SEQUENCE: 60

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Val Asp Leu Glu Ile
            20                  25                  30

Lys Arg Ala Ala Ala Glu Gln Lys Leu Ile Ser Glu Glu Asp Leu Asn
        35                  40                  45
```

<210> SEQ ID NO 61
<211> LENGTH: 175
<212> TYPE: DNA
<213> ORGANISM: Artificial Sequence
<220> FEATURE:
<221> NAME/KEY: CDS
<222> LOCATION: (35)..(166)
<220> FEATURE:
<223> OTHER INFORMATION: Description of Artificial Sequence: Vector with

```
              Histidine Tag

<400> SEQUENCE: 61
gcatgcaaaa ttctatttca aggagacagt cata atg aaa tac cta ttg cct acg        55
                                     Met Lys Tyr Leu Leu Pro Thr
                                       1               5 gca gcc gct gga ttg tta tta ctc gcg gcc cag ccg gcc atg gcc cag         103
Ala Ala Ala Gly Leu Leu Leu Leu Ala Ala Gln Pro Ala Met Ala Gln
         10                  15                  20 gtg cag ctg cag gtc ggc ctc gag atc aaa cgg gcg gcc gca cat cac         151
Val Gln Leu Gln Val Gly Leu Glu Ile Lys Arg Ala Ala Ala His His
     25                  30                  35 cat cat cac cat taa taagaattc                                           175
His His His His
 40

<210> SEQ ID NO 62
<211> LENGTH: 43
<212> TYPE: PRT
<213> ORGANISM: Artificial Sequence
<220> FEATURE:
<223> OTHER INFORMATION: Description of Artificial Sequence: Vector with
      Histidine Tag

<400> SEQUENCE: 62

Met Lys Tyr Leu Leu Pro Thr Ala Ala Ala Gly Leu Leu Leu Leu Ala
  1               5                  10                  15

Ala Gln Pro Ala Met Ala Gln Val Gln Leu Gln Val Gly Leu Glu Ile
             20                  25                  30

Lys Arg Ala Ala Ala His His His His His His
         35                  40

<210> SEQ ID NO 63
<211> LENGTH: 57
<212> TYPE: DNA
<213> ORGANISM: Artificial Sequence
<220> FEATURE:
<221> NAME/KEY: CDS
<222> LOCATION: (1)..(57)
<220> FEATURE:
<223> OTHER INFORMATION: Description of Artificial Sequence: Sequence
      across the junctions of pNIPenv

<400> SEQUENCE: 63 act gct tcg ccc ggc tcc agt gcg gcc cag ccg gcc atg gcc cag gtg         48
Thr Ala Ser Pro Gly Ser Ser Ala Ala Gln Pro Ala Met Ala Gln Val
  1               5                  10                  15 cag ctg cag                                                             57
Gln Leu Gln <210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Sequence
      across the junctions of pNIPenv

<400> SEQUENCE: 64

Thr Ala Ser Pro Gly Ser Ser Ala Ala Gln Pro Ala Met Ala Gln Val
  1               5                  10                  15

Gln Leu Gln

<210> SEQ ID NO 65
```

-continued

```
<211> LENGTH: 36
<212> TYPE: DNA
<213> ORGANISM: Artificial Sequence
<220> FEATURE:
<221> NAME/KEY: CDS
<222> LOCATION: (1)..(36)
<220> FEATURE:
<223> OTHER INFORMATION: Description of Artificial Sequence: Sequence
      across the junctions of pNIPenv

<400> SEQUENCE: 65 gtc ctc gag gag gcg gcc gca cct cat caa gtc tat                    36
Val Leu Glu Glu Ala Ala Ala Pro His Gln Val Tyr
 1               5                  10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Sequence
      across the junctions of pNIPenv

<400> SEQUENCE: 66

Val Leu Glu Glu Ala Ala Ala Pro His Gln Val Tyr
 1               5                  10

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:
      PCR primer for amplifying A31PVX

<400> SEQUENCE: 67
taatacgact cactataggg agac                                         24

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence:
      PCR primer for amplifying A31PVX

<400> SEQUENCE: 68
ggctggaggt ccgggtccac gtttgatctc cacctt                            36

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence:
      PCR primer for amplifying PVXCP

<400> SEQUENCE: 69
aaacgtggac ccggacctcc agccaacacc actcaagct                         39

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence:
      PCR primer for amplifying PVXCP
```

```
<400> SEQUENCE: 70
accgcggccg ctagttatgg tgggggtagt gaa                                     33

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence:
      PCR primer for amplifying 5T33PVXCP

<400> SEQUENCE: 71
ggctggaggt ccgggtcctt tgatttccag cttggt                                  36

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence:
      PCR primer for amplifying 5T33PVXCP

<400> SEQUENCE: 72
atcaaaggac ccggacctcc agccaacacc actcaagct                               39

<210> SEQ ID NO 73
<211> LENGTH: 92
<212> TYPE: DNA
<213> ORGANISM: Artificial Sequence
<220> FEATURE:
<223> OTHER INFORMATION: Description of Artificial Sequence:
      PCR primer for amplifying PVXCP

<400> SEQUENCE: 73
ccgaagcttg caccatgaag ttgtggctga actggatttt ccttgtaaca cttttaaatg        60
gtatccagtg tccagccaac accactcaag ct                                      92
```

The invention claimed:

1. A nucleic acid construct for delivery into mammalian cells in vivo for inducing an immune response in a patient to an antigen; comprising a construct that directs the expression of a fusion protein, said fusion protein comprising said antigen and an adjuvant, wherein said antigen is a self polypentide or an altered self polypeptide and said adjuvant is a Potato Virus X Coat Protein (PVXCP).

2. A nucleic acid construct according to claim 1 wherein said adjuvant promotes a helper T cell response.

3. A nucleic acid construct according to claim 1 or claim 2 wherein said adjuvant comprises a helper T cell epitope.

4. A nucleic acid construct according to claim 1 wherein said self polyneptide or altered self polypeptide is a tumour associated antigen.

5. A nucleic acid construct according to claim 4 wherein said tumour associated antigen is an idiotypic determinant of a T cell receptor expressed on the surface of a malignant T cell.

6. A nucleic acid construct according to claim 4 wherein said tumour associated antigen is an idiotypic determinant of a malignant B cell.

7. A nucleic acid construct according to claim 5 or claim 6 wherein said idiotypic determinant is expressed as a single chain Fv fragment.

8. A method of making a nucleic acid construct for raising an immune response in a mammal against an antigen, said method comprising: identifying a nucleic acid sequence encoding said antigen; cloning said nucleic acid sequence; and introducing the cloned nucleic acid into a vector, said vector allowing the antigen to be expressed in an mammalian cell as a fusion with an adjuvant, wherein said adjuvant is PVXCP, wherein said antigen is a self polypeptide or an altered self polypeptide.

9. A method according to claim 8 wherein said self polypeptide or altered self polypeptide is a tumour associated antigen.

10. A method of making a nucleic acid construct for treating a mammal having a B cell malignancy, said method comprising: identifying a nucleic acid sequence encoding an idiotypic determinant present on the malignant B cells of the patient by analysis of a sample of cells from the patient; cloning the nucleic acid sequence encoding the idiotypic determinant; and introducing the cloned nucleic acid into a vector, said vector allowing the idiotypic determinant to be expressed as a fusion with an adjuvant, wherein said adjuvant is PVXCP.

11. A method according to claim 8 or claim 10 wherein said plant viral coat protein comprises a helper T cell epitope.

12. A method of inducing an immune response in a patient, comprising the step of administering to said patient a nucleic acid construct according to claim 1, in a physiologically acceptable medium.

13. A method of treating a cancer patient or a patient with a predisposition to cancer, comprising the step of administering to said patient a nucleic acid construct according to claim 4 or claim 5 in a physiologically acceptable medium, wherein said tumour associated antigen associated with said cancer.

14. A method of treating a patient having a B cell malignancy, comprising the step of administering to said patient a nucleic acid construct according to claim 6 in a physiologically acceptable medium, wherein the idiotypic determinant was cloned from samples obtained from said patient.

15. A method according to claim 12, wherein the nucleic acid is unencapsidated.

16. A method according to claim 12 further comprising the step of delivering a second nucleic acid sequence to the patient, said second nucleic acid sequence encoding a further immunomodulatory polypeptide.

17. A nucleic acid construct according to claim 1 for use in a method of medical treatment.

18. A composition comprising a nucleic acid construct according to claim 1 and a physiologically acceptable diluent or carrier.

* * * * *

UNITED STATES PATENT AND TRADEMARK OFFICE
CERTIFICATE OF CORRECTION

| | |
|---|---|
| PATENT NO. | : 7,179,471 B2 |
| APPLICATION NO. | : 10/416290 |
| DATED | : February 20, 2007 |
| INVENTOR(S) | : Natalia Savelyeva et al. |

It is certified that error appears in the above-identified patent and that said Letters Patent is hereby corrected as shown below:

On the title page Item [54], after "PROTEINS", please insert --FOR INDUCING--.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,179,471 B2 | Page 1 of 1 |
| APPLICATION NO. | : 10/416290 | |
| DATED | : February 20, 2007 | |
| INVENTOR(S) | : Natalia Savelyeva et al. | |

It is certified that error appears in the above-identified patent and that said Letters Patent is hereby corrected as shown below:

On the title page Item [54] and Column 1, line 2, after "PROTEINS", please insert --FOR INDUCING--.

This certificate supersedes the Certificate of Correction issued July 14, 2009.

Signed and Sealed this

Eighteenth Day of August, 2009

David J. Kappos
*Director of the United States Patent and Trademark Office*